(12) United States Patent
Wang

(10) Patent No.: US 9,598,738 B2
(45) Date of Patent: Mar. 21, 2017

(54) **METHOD FOR PRODUCING SEGMENTAL ANEUPLOIDY (SAN) STRAINS OF *TRICHODERMA REESEI* VIA SEXUAL CROSSING AND SAN STRAINS PRODUCED THEREFROM**

(71) Applicant: Academia Sinica, Taipei (TW)

(72) Inventor: Ting-Fang Wang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/027,032

(22) PCT Filed: Oct. 1, 2014

(86) PCT No.: PCT/US2014/058654
§ 371 (c)(1),
(2) Date: Apr. 4, 2016

(87) PCT Pub. No.: WO2015/051012
PCT Pub. Date: Apr. 9, 2015

(65) Prior Publication Data
US 2016/0237509 A1      Aug. 18, 2016

Related U.S. Application Data

(60) Provisional application No. 61/886,043, filed on Oct. 2, 2013.

(51) Int. Cl.
*C12N 1/15* (2006.01)
*C12Q 1/68* (2006.01)
*C12N 1/14* (2006.01)

(52) U.S. Cl.
CPC ............ *C12Q 1/6895* (2013.01); *C12N 1/14* (2013.01)

(58) Field of Classification Search
None
See application file for complete search history.

(56) References Cited

FOREIGN PATENT DOCUMENTS

WO      WO 2014/102241 A1      7/2014

OTHER PUBLICATIONS

Gruber et al., Comparative analysis of the repertoire of G protein-coupled receptors of three species of the fungal genus Trichoderma. BMC Microbiol. May 16, 2013;13:108. doi: 10.1186/1471-2180-13-108.
Martinez et al., Genome sequencing and analysis of the biomass-degrading fungus Trichoderma reesei (syn. Hypocrea jecorina). Nat Biotechnol. May 2008;26(5):553-60. doi: 10.1038/nbt1403. Epub May 4, 2008. Erratum in: Nat Biotechnol. Oct. 2008;26(10):1193.. Barbote, Ravi [corrected to Barabote, Ravi].
Seidl et al., The Hypocrea jecorina (Trichoderma reesei) hypercellulolytic mutant RUT C30 lacks a 85 kb (29 gene-encoding) region of the wild-type genome. BMC Genomics. Jul. 11, 2008;9:327. doi:10.1186/1471-2164-9-327.
Steiger et al., Transformation system for Hypocrea jecorina (Trichoderma reesei) that favors homologous integration and employs reusable bidirectionally selectable markers. Appl Environ Microbiol. Jan. 2011;77(1):114-21. doi: 10.1128/AEM.02100-10. Epub Nov. 12, 2010.
Vitikainen et al., Array comparative genomic hybridization analysis of Trichoderma reesei strains with enhanced cellulase production properties. BMC Genomics. Jul. 19, 2010;11:441. doi: 10.1186/1471-2164-11-441.

*Primary Examiner* — Jim Ketter
(74) *Attorney, Agent, or Firm* — Wolf, Greenfield & Sacks, P.C.

(57) ABSTRACT

The present invention relates to a technology to provide segmental aneuploidy progeny strains of *Trichoderma reesei*. In particular, the present invention relates to a method to produce segmental aneuploidy progeny strains of *Trichoderma reesei* via sexual crossing of two parent haploid strains with chromosome heterozygosity (e.g. one having scaffold M and scaffold 33, the other having scaffold F and scaffold X), preferably at least one of which includes a non-homologous end joining (NHEJ) gene. The present invention also relates to stable, segmental aneuploidy progeny strains of richoderma reesei thus produced which particularly exhibit enhanced gene expression or activities of carbohydrate-active enzymes (CAZymes) and more particularly prevent returning to euploidy for an extended period of time.

22 Claims, 16 Drawing Sheets

A

B

A

B

SEQUENCE LISTING

```
<160> NUMBER OF SEQ ID NOS: 23

<210> SEQ ID NO 1
<211> LENGTH: 18
<212> TYPE: DNA
<213> ORGANISM: Artificial Sequence
<220> FEATURE:
<223> OTHER INFORMATION: Primer A

<400> SEQUENCE: 1
cttccagcct aagtactc                                                   18

<210> SEQ ID NO 2
<211> LENGTH: 19
<212> TYPE: DNA
<213> ORGANISM: Artificial Sequence
<220> FEATURE:
<223> OTHER INFORMATION: Primer B

<400> SEQUENCE: 2
gtcgatcgtg ctaatgaag                                                  19

<210> SEQ ID NO 3
<211> LENGTH: 18
<212> TYPE: DNA
<213> ORGANISM: Artificial Sequence
<220> FEATURE:
<223> OTHER INFORMATION: Primer C

<400> SEQUENCE: 3
caaggctatt atccgcag                                                   18

<210> SEQ ID NO 4
<211> LENGTH: 18
<212> TYPE: DNA
<213> ORGANISM: Artificial Sequence
<220> FEATURE:
<223> OTHER INFORMATION: Primer D

<400> SEQUENCE: 4
ctctgagggg attagaag                                                   18

<210> SEQ ID NO 5
<211> LENGTH: 547
<212> TYPE: DNA
<213> ORGANISM: Trichoderma atraviride

<400> SEQUENCE: 5
caaggctatt atccgcagtg ggacaattgt gctttgatgt tggttcgctc tacactgggt      60
caaacatgaa caggcagtgg aggggggtgt gatgagaatg aaaccaagag ccaacctgtg     120
gatcaatttc aacgtggggc gatgtgcatg tagggactcc gaagtgtttt cgggacggaa     180
ccggcctaaa caagaccatg ttcgacggtt tattaagcag gcaaatatcg acaggcatgg     240
cgtatgtcaa gacctaatca atcattgtcc tggtgaggcc tatacctgcc gttgtggaaa     300
```

```
gatactcgcg atgtattttt tcttctgtc tctgtcatcg atacttgcct actggatcat    360
caagacggcc gtctcttcaa acaaagatcg actttatgcc cgccgaaaag catgtcaacc    420
ctgcgcgcgc ctaccacaaa ctgaaagggt cattggctat tctttgttca agcaagatgc    480
taccattgca cgccagggga ggtccttgca aacagcccaa gaccgcttcc gtttgctcgg    540
tgacacg                                                             547
```

<210> SEQ ID NO 6
<211> LENGTH: 467
<212> TYPE: DNA
<213> ORGANISM: Trichoderma atraviride

<400> SEQUENCE: 6

```
cttccagcct aagtactctg ctaaagggcg tatcttgtaa tgtatacttt aactgttact     60
gcattgtaaa gccaaacact gcgggcttcc atatgggaaa ttgatctatc tcaatagcgc    120
tcagtaggta cgaagagtag gcatccctcg agacaaaccc tcctccacga gcccctcaag    180
tggtaggtag ttcaggtgca ctctgcacga acgctgactg cacatcagac gcacttggtg    240
ctgattctcg ctgcagagga gtgaggtacc cgtatcaccc tactccaatc gcctgagaag    300
cttgtatctt gctcaacatt ccggagcagc acctacatgt actacatgtg aatcgcccta    360
tatctcattc tgaccggaga acgagacagc acccacgtat tcataccctat ttactttctt    420 ctgttttta cctcttctcg atcttctttt cttctaatcc cctcaga                 467
```

<210> SEQ ID NO 7
<211> LENGTH: 462
<212> TYPE: DNA
<213> ORGANISM: Trichoderma atraviride

<400> SEQUENCE: 7

```
cttccagcct aagtactctg ctaaagggcg tatcttgtaa tgtatacttt aactgttact     60
gcattgtaaa gccaaacact gcgggcttcc atatgggaaa ttgatctatc tcaatagcgc    120
tcagtaggta cgaagagtag gcatccctcg agacaaaccc tcctccacga gcccctcaag    180
tggtaggtag ttcaggtgca ctctgcacga acgctgactg cacatcagac gcacttggtg    240
ctgattctcg ctgcagagga gtgaggtacc cgtatcaaga cggccgtctc ttcaaacaaa    300
gatcgacttt atgcccgccg aaaagcatgt caaccctgcg cgcgcctacc acaaactgaa    360
agggtcattg gctattcttt gttcaagcaa gatgctacca ttgcacgcca ggggaggtcc    420
ttgcaaacag cccaagaccg cttccgtttg ctcggtgaca cg                     462
```

<210> SEQ ID NO 8
<211> LENGTH: 552
<212> TYPE: DNA
<213> ORGANISM: Trichoderma atraviride

<400> SEQUENCE: 8

```
caaggctatt atccgcagtg ggacaattgt gctttgatgt tggttcgctc tacactgggt     60
caaacatgaa caggcagtgg aggggggtgt gatgagaatg aaaccaagag ccaacctgtg    120
gatcaatttc aacgtggggc gatgtgcatg tagggactcc gaagtgtttt cgggacggaa    180
ccggcctaaa caagaccatg ttcgacggtt tattaagcag gcaaatatcg acaggcatgg    240
cgtatgtcaa gacctaatca atcattgtcc tggtgaggcc tatacctgcc gttgtggaaa    300
gatactcgcg atgtattttt tcttctgtc tctgtcatcg atacttgcct actggatcat    360
caccctactc caatcgcctg agaagcttgt atcttgctca acattccgga gcagcaccta    420
```

```
catgtactac atgtgaatcg ccctatatct cattctgacc ggagaacgag acagcaccca    480
cgtattcata cctatttact ttcttctgtt ttttacctct tctcgatctt cttttcttct    540
aatcccctca ga                                                        552

<210> SEQ ID NO 9
<211> LENGTH: 304
<212> TYPE: DNA
<213> ORGANISM: Artificial Sequence
<220> FEATURE:
<223> OTHER INFORMATION: Probe

<400> SEQUENCE: 9
agctacatga gatcctgcat accgtatctt tgtcctggta aactattgtt tcgtagttca     60
agaggacatt ctgaaggaac accgagagca tttcttccag cctaagtact ctgctaaagg    120
gcgtatcttg taatgtatac tttaactgtt actgcattgt aaagccaaac actgcgggct    180
tccatatggg aaattttctt atttcaatag cgctcagtag gtacgaagag taggcatccc    240
tcgagacaaa ccctcctcca cgagcccctc aagtggtagg tagttcaggt gcactctgca    300
cgaa                                                                 304

<210> SEQ ID NO 10
<211> LENGTH: 20
<212> TYPE: DNA
<213> ORGANISM: Artificial Sequence
<220> FEATURE:
<223> OTHER INFORMATION: PA7543 primer

<400> SEQUENCE: 10
agctacatga gatcctgcat                                                 20

<210> SEQ ID NO 11
<211> LENGTH: 20
<212> TYPE: DNA
<213> ORGANISM: Artificial Sequence
<220> FEATURE:
<223> OTHER INFORMATION: A7544 primer

<400> SEQUENCE: 11
tcaggtgcac tctgcacgaa                                                 20

<210> SEQ ID NO 12
<211> LENGTH: 443
<212> TYPE: DNA
<213> ORGANISM: Trichoderma atraviride

<400> SEQUENCE: 12
ttaaatccca caactaccta ttactacatg tacatttgat caattgcaag ccgtgaccga     60
gctacatgag atcctgcata ccgtatcttt gtcctggtaa actattgttt cgtagttcaa    120
gaggacattc tgaaggaaca ccgagagcat ttcttccagc ctaagtactc tgctaaaggg    180
cgtatcttgt aatgtatact ttaactgtta ctgcattgta aagccaaaca ctgcgggctt    240
ccatatggga aattttctta tttcaatagc gctcagtagg tacgaagagt aggcatccct    300
cgagacaaac cctcctccac gagcccctca agtggtaggt agttcaggtg cactctgcac    360
gaacgctgac cgcacatcag acgcacttgg tgctgattct cgctgcagag gagcgaggta    420
cccctatcaa gacggccgtc tct                                            443

<210> SEQ ID NO 13
```

```
<211> LENGTH: 1512
<212> TYPE: DNA
<213> ORGANISM: Trichoderma atraviride

<400> SEQUENCE: 13
ttaaatccca caactaccta ttactacatg tacatttgat caattgcaag ccgtgaccga      60
gctacatgag atcctgcata ccgtatcttt gtcctggtaa actattgttt cgtagttcaa     120
gaggacattc tgaaggaaca ccgagagcat ttcttccagc ctaagtactc tgctaaaggg     180
cgtatcttgt aatgtatact ttaactgtta ctgcattgta aagccaaaca ctgcgggctt     240
ccatatggga aattttctta tttcaatagc gctcagtagg tacgaagagt aggcatccct     300
cgagacaaac cctcctccac gagcccctca agtggtaggt agttcaggtg cactctgcac     360
gaacgctgac cgcacatcag acgcacttgg tgctgattct cgctgcagag gagcgaggta     420
cccctatcac cctactccaa tcgcctgaga agcttgtatc ttgctcaaca ttccggagca     480
gcacctacat gtactacatg tgaatcgccc tatatctcat tctgaccggc gaacgagaca     540
gcacccacca cgtattcatg cctatttact ttcttctgta ttttacctct tctcgatctt     600 ctttcttct aatcccctca gagcctcaac aacctccacc tctttctgca tcagcacacg     660
agtgacatcc tgcatcttcc acaccatcag atacgttggg cctccttta agaaagctac     720 aaaacttgta agaaatcttc acttaaggta ctgagaggtt cttgtttctt tatgctacag     780
tccttcgaga taactgacac atagtgtttc attcagcatc gcttccattg cgctcgtttt     840
ctcggctcac ctcaaagaca tctcagccat cttggaggcc aagagcaaga tatcaaacaa     900
tcttctcttt gaactggtgg caatgagcag cgatagctat tggattgttc ctcctcaacc     960
cccgggtggt ggcacgtgga aaggctgtgc tctgctcaag aagccagatg gaggagattt    1020
cgtgctattt tctcccaatg ccgtgcatct gagtgcgatg ctccaggtgc atgacgcgca    1080
ccaagcatct gtcgtcagta atgcatctca gtcgacctca caagacaatg agatgactga    1140
gttcatggta atgggacgat gcagacattt gttggatggc tattcgcaca cgaaccctca    1200
aagctcatcc ggacaaatgg cagagagctt gaacaggcta catgccgatt tgaaaggaac    1260
aaggtcccga gggcagaagt tcatcactgc agcatacgtc ggcttcgact cctgcatgca    1320
gggtcctgtc tttgccaggg cggctaaaga tgcggccagc tccaaccccct ccaaatcgat    1380 cgcttcgaat gaagcaaatc agtcaagagg gtcaaacggt atccttgacc tgaaggatct    1440
gagcttcagt tgtggctctg cgtcctcttc tgtgggactg ggattcattc cacattatgc    1500
agtaacgtct cg                                                        1512

<210> SEQ ID NO 14
<211> LENGTH: 18
<212> TYPE: DNA
<213> ORGANISM: Artificial Sequence
<220> FEATURE:
<223> OTHER INFORMATION: tact1 forward primer

<400> SEQUENCE: 14
atgatcggta tgggtcag                                                    18

<210> SEQ ID NO 15
<211> LENGTH: 18
<212> TYPE: DNA
<213> ORGANISM: Artificial Sequence
<220> FEATURE:
<223> OTHER INFORMATION: tact1 reverse primer

<400> SEQUENCE: 15
```

```
gatgtcacgg acgatttc                                          18
```

<210> SEQ ID NO 16
<211> LENGTH: 18
<212> TYPE: DNA
<213> ORGANISM: Artificial Sequence
<220> FEATURE:
<223> OTHER INFORMATION: mat1-1 forward primer

<400> SEQUENCE: 16

```
agccgagata cctcaatg                                          18
```

<210> SEQ ID NO 17
<211> LENGTH: 18
<212> TYPE: DNA
<213> ORGANISM: Artificial Sequence
<220> FEATURE:
<223> OTHER INFORMATION: mat1-1 reverse primer

<400> SEQUENCE: 17

```
acctgtcctc caatcttc                                          18
```

<210> SEQ ID NO 18
<211> LENGTH: 18
<212> TYPE: DNA
<213> ORGANISM: Artificial Sequence
<220> FEATURE:
<223> OTHER INFORMATION: mat1-2 forward primer

<400> SEQUENCE: 18

```
tcagtcaacg cagtcatg                                          18
```

<210> SEQ ID NO 19
<211> LENGTH: 16
<212> TYPE: DNA
<213> ORGANISM: Artificial Sequence
<220> FEATURE:
<223> OTHER INFORMATION: mat1-2 reverse primer

<400> SEQUENCE: 19

```
cattggcaca agcgac                                            16
```

<210> SEQ ID NO 20
<211> LENGTH: 21
<212> TYPE: DNA
<213> ORGANISM: Artificial Sequence
<220> FEATURE:
<223> OTHER INFORMATION: tku70 forward primer

<400> SEQUENCE: 20

```
caggagactc caagtttgat c                                      21
```

<210> SEQ ID NO 21
<211> LENGTH: 18
<212> TYPE: DNA
<213> ORGANISM: Artificial Sequence
<220> FEATURE:
<223> OTHER INFORMATION: tku70 reverse primer

<400> SEQUENCE: 21

```
tgctgcgctt cttgaatc                                          18
```

<210> SEQ ID NO 22
<211> LENGTH: 20
<212> TYPE: DNA

```
<213> ORGANISM: Artificial Sequence
<220> FEATURE:
<223> OTHER INFORMATION: tmu53 forward primer

<400> SEQUENCE: 22
gagataggtg tagtccttgg                                            20

<210> SEQ ID NO 23
<211> LENGTH: 20
<212> TYPE: DNA
<213> ORGANISM: Artificial Sequence
<220> FEATURE:
<223> OTHER INFORMATION: tmu 53 reverse primer

<400> SEQUENCE: 23
gagaagacgt tcctatacct                                            20
```

METHOD FOR PRODUCING SEGMENTAL ANEUPLOIDY (SAN) STRAINS OF *TRICHODERMA REESEI* VIA SEXUAL CROSSING AND SAN STRAINS PRODUCED THEREFROM

RELATED APPLICATIONS

This application is a national stage filing under 35 U.S.C. §371 of international PCT application PCT/US2014/058654, filed Oct. 1, 2014, which claims the benefit of U.S. provisional application number 61/886,043, filed Oct. 2, 2013 under 35 U.S.C. §119, the entire content of which is incorporated by reference herein.

TECHNOLOGY FIELD

The present invention relates to a technology to produce segmental aneuploidy progeny strains of *Trichoderma reesei*. In particular, the present invention relates to a method to produce segmental aneuploidy progeny strains of *Trichoderma reesei* via sexual crossing of two parent haploid strains with chromosome heterozygosity, especially either of which further includes deletion of a non-homologous end joining (NHEJ) gene. The present invention also relates to stable, segmental aneuploid progeny strains of *Trichoderma reesei* thus produced, which can exhibit enhanced gene expression or activities of carbohydrate-active enzymes (CAZymes) and more particularly prevent returning to euploidy for an extended period of time.

BACKGROUND OF THE INVENTION

Fungi of the genus *Trichoderma* are present in soils as well as in other diverse habitats. They are beneficial symbiotic partners for plants, particularly crops. *Trichoderma* spp. secrete cellulases and hemicellulases to degrade β-glucan and xylan, the key structural components of lignocellulosic biomass, into glucose and xylose, respectively. Several high-enzyme-producing strains (e.g., QM9414, Rut-C30) in use today have been generated from *Trichoderma reesei* QM6a strain by treatments with chemical mutagens and/or radiation and widely used for industrial applications. However, due to multiple rounds of chemical and/or physical mutagenesis, the genomes of these hypersecretion mutants have plenty of mutations, deletions and rearrangements [1-3], which cause genome instability. Further, these industrial strains secret less xylan-degrading hemicellulases than β-glucan-degrading cellulases.

*T. reesei* is the anamorph of the pantropical ascomycete *Hypocrea jecorina* [4]. *H. jecorina* CBS999.97 wild isolate undergoes a heterothallic reproductive cycle, and generates CBS999.97(1-1) and CBS999.97(1-2) haploids with MAT1-1 and MAT1-2 mating-type loci, respectively. QM6a has a MAT1-2 mating type locus and can also mate with the CBS999.97(1-1) haploid to form fruiting bodies that contain asci with 16-part ascospores [5].

Meiosis is a special type of cell division that gives rise to genetic diversity in sexually reproductive organisms. Programmed DNA double-strand breaks (DSBs) are spontaneously generated throughout the genome by the meiosis-specific Spo11 endonucleases [6]. In model organisms like yeast and mouse, the Spo11-induced DSBs are repaired robustly by error-free homologous recombination to ensure accurate segregation of homologous chromosomes and genome stability. By contrast, previous studies have revealed that aneuploid or segmentally aneuploid (SAN) meiotic products are generated in some filamentous fungi. For example, in the fungal human pathogen *Cryptococcus neoformans*, a large segmental duplication occurs during meiosis via telomere-telomere fusion and chromosomal translocation between two different chromosomes [7,8]. The plant-pathogenic fungus *Mycosphaerella graminicola* (anamorph *Septoria tritici*) generates ascospores with up to eight dispensable chromosomes [9,10]. Some ascospore isolates of the plant-pathogenic fungus *Nectria haematococca* mating population VI (anamorph *Fusarium solani*) contain "extra" chromosomes, called "conditionally dispensable" chromosomes [11-13]. *Nectria haematococca* mating population VI is notable also for being a genetically close species of *T. reesei* in the order *Hypocreales* [13,14].

There is still a need to develop a technology to obtain new strains of *T. reesei* that exhibit enhanced expression or activities of carbohydrate degrading enzymes, especially hemicellulases.

BRIEF SUMMARY OF THE INVENTION

In this invention, it is unexpected found that viable segmentally aneuploid progeny can be produced by sexual production between two haploid *T. reesei* strains with chromosome heterozygosity (one having scaffold M and scaffold 33, the other having scaffold F and scaffold X) during meiosis and post-meiotic mitosis, wherein such resultant SAN progeny includes duplication of a chromosomal segment of about 500 Mbp in length (i.e. D segment as described below) that enhances expression or activities of a variety of carbohydrate degrading enzymes. It is also found that deletion of one nonhomologous end-joining (NHEJ) gene (tku70 or ligase IV tmus53) can stabilize segmental duplication, i.e. preventing the SAN progeny turning back to euploidy, indicating that NHEJ but not homologous recombination is responsible for restoration of euploidy. We have therefore applied the technology to generate stable SAN strains that produce more hemicellulases than RUT-C30, a widely used industrial strain for lignocellulosic biomass degradation.

Accordingly, in one aspect, the present invention provides a method for preparing a segmental aneuploid strain of *Trichoderma reesei* comprising steps of:
(a) identifying and choosing a first strain being *Trichoderma reesei*, which is mating competent and carries scaffold 33 and scaffold M in its genome;
(b) identifying and choosing a second strain being *Trichoderma reesei*, which is mating competent, capable of mating with the first strain of step (a), and carries scaffold F and scaffold X in its genome;
(c) sexually crossing the first strain of step (a) with the second strain of step (b); and
(d) identifying and selecting a segmental aneuploid (SAN) progeny from step (c) that has duplication of the D segment in its genome.

In some embodiments, the first strain has a MAT1-1 locus and the second strain has a MAT1-2 locus, or the first strain has a MAT2-2 locus and the second strain has a MAT1-1 locus.

In certain embodiments, in step (a), the first strain is identified by conducting a polymerase chain reaction (PCR) analysis to determine the presence of scaffold 33 and scaffold M, in its genome.

In certain embodiments, in step (b), the second strain is identified by conducting a polymerase chain reaction (PCR) analysis to determine the presence of scaffold F and scaffold X, in its genome.

In some embodiments, in step (d), the SAN progeny is identified by a comparative genomic hybridization (CGH) analysis or a Southern blot analysis to determine duplication of the D segment.

In particular embodiments, the SAN progeny exhibits enhanced gene expression of one or more genes encoding a carbohydrate-active enzyme (CAZyme).

In some embodiments, the first strain or the second strain further includes deletion of a non-homologous end joining (NHEJ) gene, such that the resultant SAN progeny, produced from sexual crossing of the first strain and the second strain, having duplication of the D segment and deletion of the NHEJ gene in its genome, is identified and selected.

In certain examples, the NHEJ gene is tku70 or tmus53.

In still another aspect, the present invention provides a method of producing a stable, segmentally aneuploid strain of *Trichoderma reesei*, comprising:
(a) sexually crossing two haploid mating competent strains of *Trichoderma reesei* with chromosome heterozygosity, wherein at least one of the two strains includes deletion of a NHEJ gene; and
(b) identifying and selecting a progeny from step (a) that is segmental aneuploid (SAN) and has deletion of the NHEJ gene.

Also provided is a stable, segmentally aneuploid strain of *Trichoderma reesei* obtained by the method as describe herein.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 8(A) Schema illustrating the location of PCR primers (A, B, C and D) used for the genotyping scaffold (M, F, 33 and X), respectively. FIG. 8(B) PCR genotyping of indicated haploid strains. CBS999.97(1-1), CBS999.97(1-2) and QM6a were used as controls. Two new haploids, CBS999.97(1-1, M, 33) and CBS999.97(1-2, F, X), were identified from the offspring of the two parental haploids, CBS999.97(1-1, F, X) and CBS999.97(1-2, M, 33). We found that all 16 ascospores generated from sexually crossing CBS999.97(1-2, F, X) with CBS999.97(1-2, F, X) or crossing CBS999.97(1-1, M, 33) with CBS999.97(1-2, M, 33) were viable. Moreover, deletion of either tku70 or tmus53 did not affect meiosis, ascospore number or ascospore viability in any of the relevant strains. See also Table 6 in Example 2.2.

FIG. 9 shows the CGH results in scaffold M (27+28+36) and scaffold 33 of the two parental CBS999.97 strains, 3 viable segmentally aneuploid (SAN) ascospores, 1 viable euploid ascospores and two return-to-euploid (RTU) strains, indicating that the L segment is absent in the viable segmentally aneuploid (SAN) ascospores. The CGH results in scaffold M (27+28+36) and scaffold 33 of the two parental CBS999.97 strains, 3 viable segmentally aneuploid (SAN) ascospores, 1 viable euploid ascospores and two return-to-euploid (RTU) strains. The 3 SAN ascospores that contain two D segments lose the L segment, whereas the 2 RTU strains have a D segment and no L segment.

Figure 10:
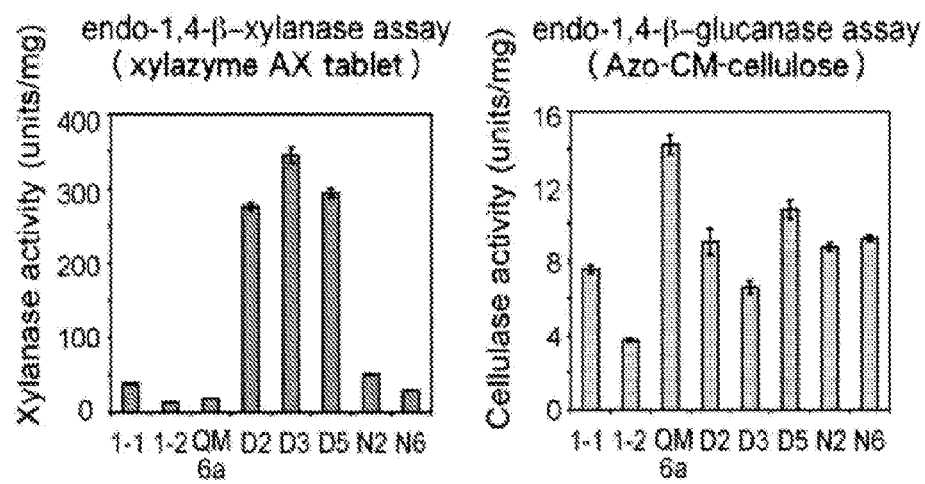
Figure 10:
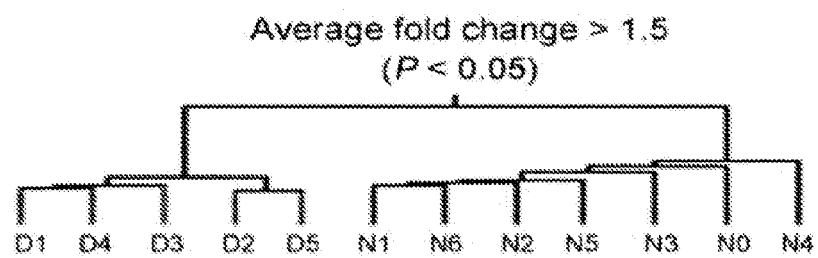
Figure 10:
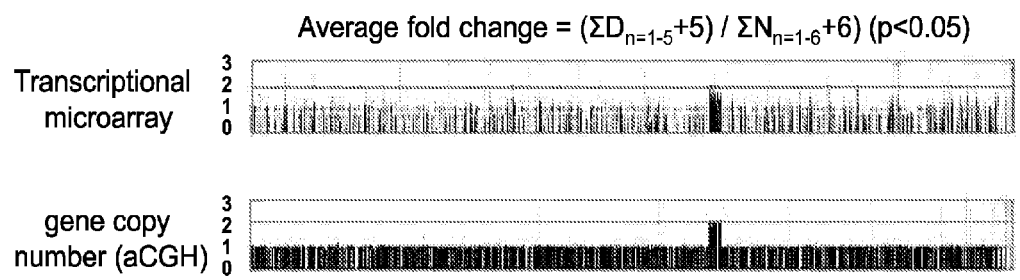

FIG. 10 shows that segmentally aneuploid (SAN) progeny produce higher levels of xylanases. (A) Xylanase and cellulase specific activities (U/mg of mycelium) of indicated strains were measured using the xylazyme AX tablet and the Azo-CM-cellulose as substrates, respectively. Experiments were conducted in triplicates and are presented with standard deviations. (B) Comparison of genome-wide transcriptional profiles, generated from a heatmap, in 5 strains with duplicated segments (D1-D5) and seven euploid control strains (N0-N6) (P<0.05). The Gene Expression Omnibus accession number is GSE-41965. (C) Impact of gene copy number on global transcription. Average ratios of genome-wide mRNA levels (upper panel) and gene copy number (lower panel) in five strains with segmental duplication (D1-D5) and seven euploid control strains (N1-N6) are shown. All measurements were carried out in triplicate (P<0.05).

Figure 11:
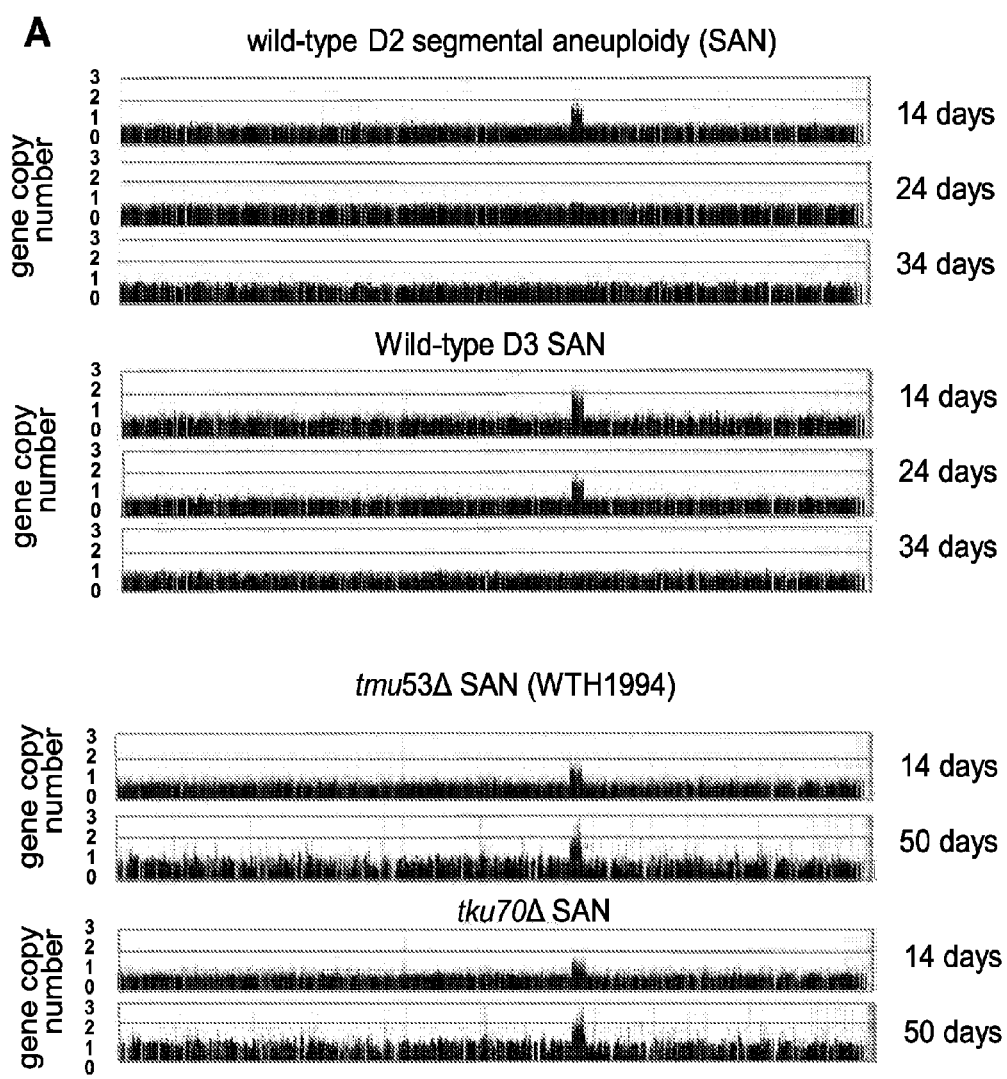
Figure 11:
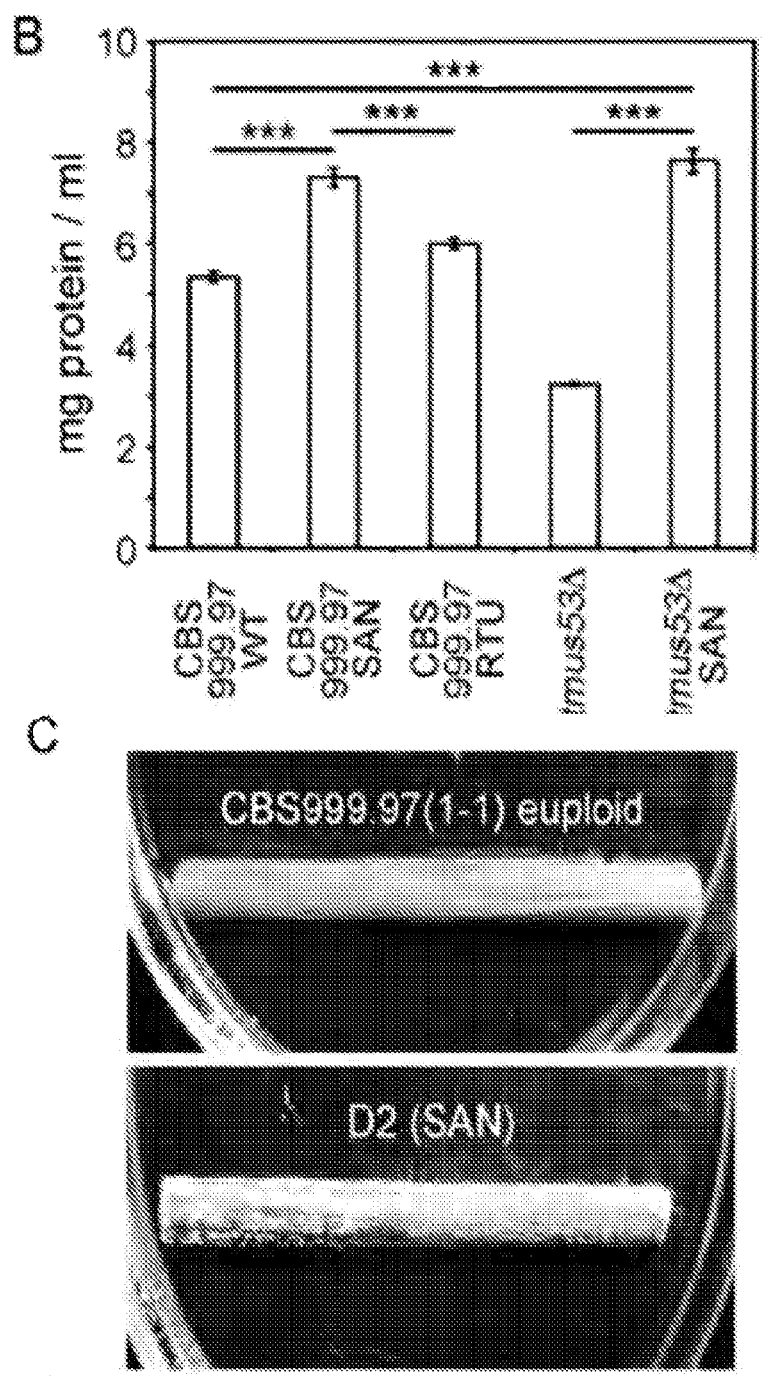
Figure 11:
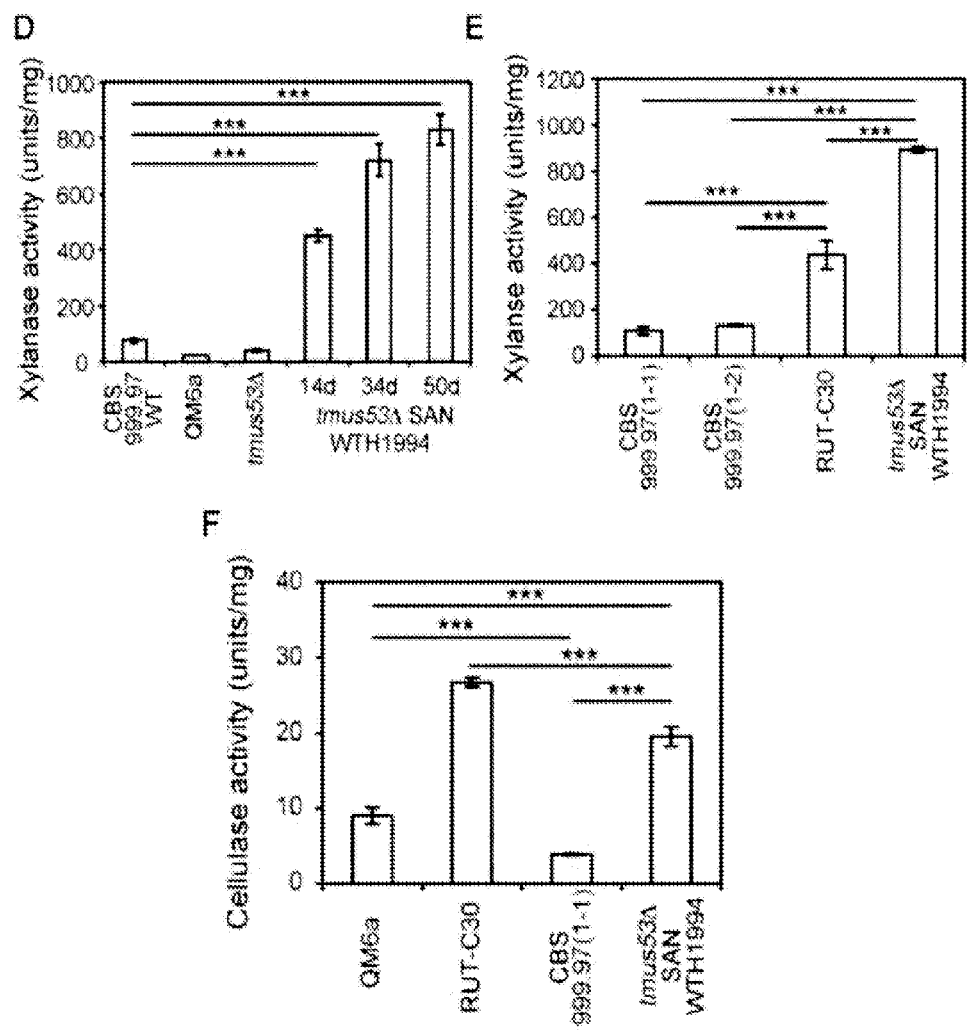

FIG. 11 shows that loss of the NHEJ gene stabilizes segmental duplication and thus enhances growth advantage. (A) The aCGH results of two wild-type SAN (D2, D3), tku70Δ SAN and tmus53ΔSAN (WTH1994) progeny. The numbers of days post ascospore germination in a dextrose-containing malt extract agar (MEA) medium are indicated on the right. The Gene Expression Omnibus accession number is GSE-42359. (B) The SAN strains produced more biomass than the CBS999.97 euploid strains or the return-to-euploid (RTU) strains in a xylan-based Mandels Androeotti medium. Experiments were conducted with two different colonies each in triplicates and are presented with mean values±SEM (error bars). (C) The SAN (D2) mutant grew better than the parental euploid strain on rice straw. (D) The Δmus53 SAN (WTH1994) strain maintained high levels of xylanase activity up to 50 days. (E, F) Compared to RUT-C30, a widely used hypersecretion mutant of $T.$ $reesei$, the tmus53Δ SAN mutant (WTH1994) shows ~2-fold specific xylanase activity and ~0.8-fold specific cellulase activity. Experiments were conducted in triplicates and are presented with mean values ±SEM (error bars).

Figure 12:
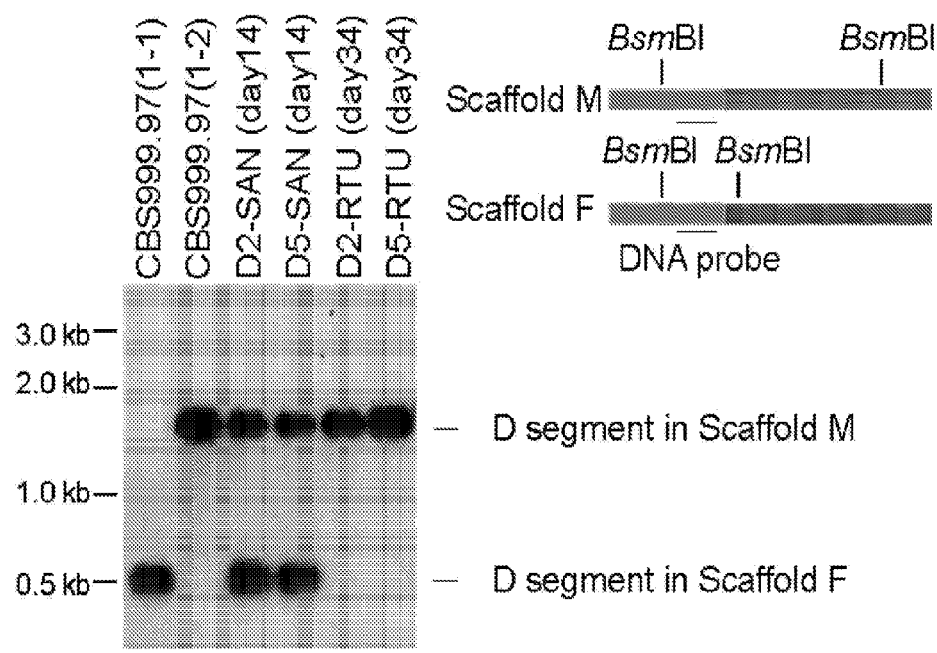

FIG. 12 shows the Southern blot analysis of the two D segments before and after RTU. The location of the BsmBI restriction enzyme sites and the DNA probe used for Southern blot analysis is indicated in the right panel. The restriction fragments of the D segments in scaffold F and scaffold M are ~400-bp and ~1500-bp in length, respectively. The two parental haploid strains, CBS999.97(1-1) and CBS999.97(1-2), were used as positive controls.

DETAILED DESCRIPTION OF THE INVENTION

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "about" or "approximately" or "around" as used herein means within ±20%, preferably within ±15%, more preferably within ±10%, and most preferably within ±5% of a given value or range.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "euploid" refers to the normal set of chromosomes that is characteristic for a given species. The term "segmental aneuploidy" refers to a state in the genome of an organism in which some chromosome segments are present in abnormal copy numbers, such as duplications in certain areas of a chromosome.

As known in the art, regarding genomic sequencing, the primary sequence data are short sequence reads. Many of these sequences overlap with each other and can be combined to produce a longer contiguous sequence, i.e. contig. Adjacent contigs can be oriented, ordered and connected together into larger scaffolds, which can be generally positioned on chromosomes. *T. reesei* QM6a has been reported to have 89 scaffolds (sets or order and oriented contigs) to generate around 34 Mbp genomic sequences [1]. The genomic sequence is available at the *T. reesei* genome database v2.0 (http://genome.jgi-psf.org/Trire2/Trire2.home.html) at the Joint Genome Institute, USA.

As used herein, the term "homologous recombination" means the exchange of DNA fragments between two DNA molecules or chromatids at the region with homologous nucleotide sequences.

As used herein, the term "homologous" means a structural feature of a DNA sequence that has at least about 70% sequence identity as compared to a reference sequence, particularly at least about 85%sequence identity, more particularly at least about 95%sequence identity, and still more particularly about 99% sequence identity, and most preferably about 100% sequence identity as compared to a reference sequence. It is understandable that homologous sequences can have insertions, deletions and substitutions in the nucleotide sequence. Therefore, liner sequences of nucleotides can be essentially identical to each other even if some of the nucleotide residues do not exactly correspond or align. The reference sequence may be a subset of a larger sequence, such as a portion of a gene or flanking sequence, or a repetitive portion of a chromosome.

To determine the percent identity of two nucleotide or amino acid sequences, the sequences are aligned for optimal comparison purposes (e.g., gaps can be introduced in the sequence of a first sequence for optimal alignment with a second sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

As used herein, the term "sexual crossing" in connection with fungi can mean crossing between donor fungus and acceptor fungus, which are mating competent. The donor fungus and acceptor fungus are normally of the same species but different with respect to their mating type (MAT) locus or gene encoding putative mating type idiomorphs and/or sex-genes. For example, the donor fungus may have one type of MAT locus and the acceptor fungus may have the opposite type of MAT locus, wherein the donor MAT locus of the donor is able to complement the MAT locus of the acceptor fungus in order to confer a sexual cycle to the acceptor fungus. Typically, filamentous ascomycete fungi can have two mating types, MAT1-1 and MAT1-2, and therefore for example sexual crossing can occur between a first strain having a MAT1-1 locus with a second strain having a complementary locus i.e. the MAT1-2 locus.

The present invention provides a technology to produce segmental aneuploid progeny strains of *Trichoderma reesei* via sexual crossing and the strains thus produced.

In one aspect, the present invention provides a method for producing segmental aneuploidy progeny strains of *Trichoderma reesei*, which comprises identifying and choosing two parent mating competent haploid strains with chromosome heterozygosity, e.g. one having scaffold M and scaffold 33, the other having scaffold F and scaffold X, then sexual crossing of these two parent strains, and identifying and selecting a segmental aneuploid progeny from the sexual crossing that has duplication of the D segment in its genome.

Figure 6:
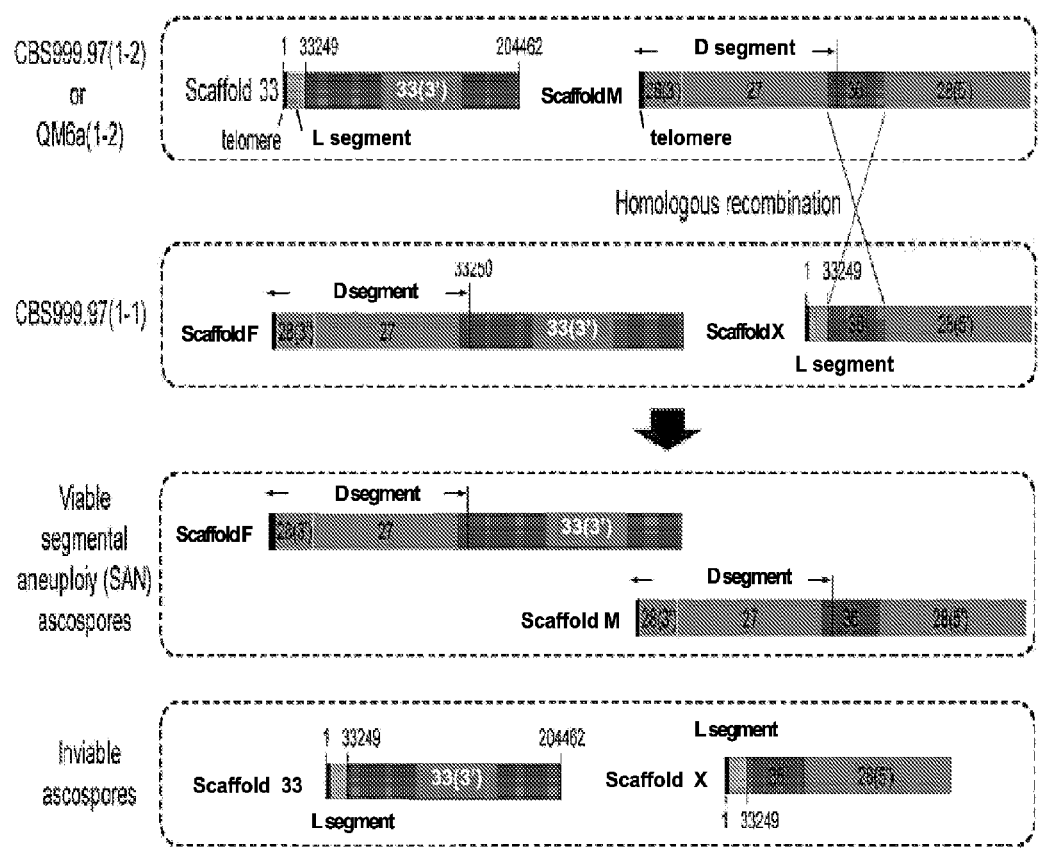
FIG. 6 shows hypothetical model of the formation of viable SAN ascospore and inviable ascospore via homologous recombination during meiosis. The Chromosome heterozygosity facilitates the formation of segmental aneuploidy.
Figure 7:
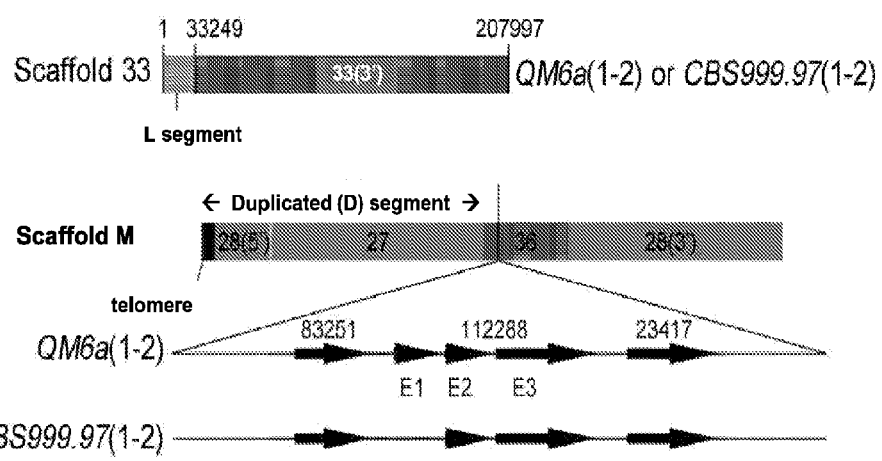
FIG. 7 shows differential chromosomal organization in QM6a and CBS999.97 genomes. (A) Scaffold 33 and scaffold M in the QM6a and wild isolate CBS999.97(1-2) genomes. Scaffolds 27, 28, 33 and 36 are indicated by arrows in cyan, blue, dark grey and green, respectively. Scaffold 28 is located near a telomere (in black), because the 3' terminus of scaffold M is connected to a repeated hexanucleotide sequence, TTAGGG, which is the telomeric repeat of QM6a. The 5' terminus of scaffold (L segment) is indicated in light grey. The three exons (E1, E2, E3) of a novel gene (ID: 112288) are indicated. The first exon (E1) only exists in the QM6a genome. (B) Scaffold F and scaffold X in the wild isolate CBS999.97(1-1) genomes.
Figure 7:
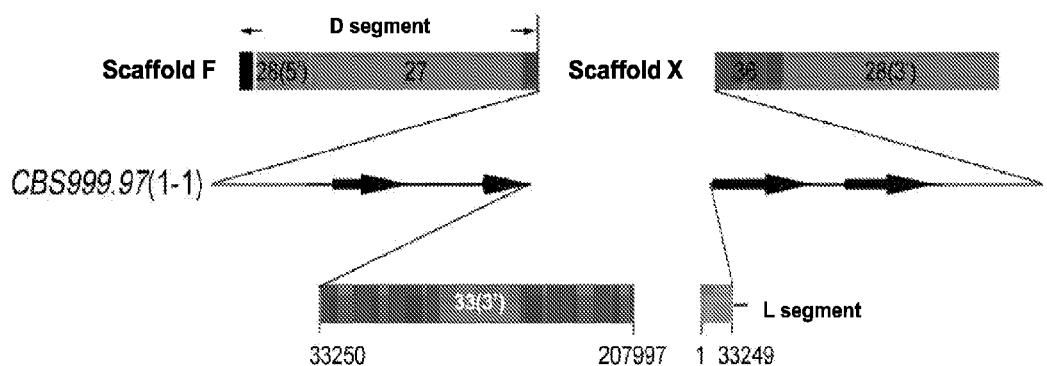

As described herein, scaffolds M, 33, F and X and D segment present in the genome of *Trichoderma reesei* (QM6a and CBS999.97) are as shown in FIG. 6 and FIG. 7.

Specifically, as used herein, scaffold 33 comprises:
(i) 5' terminus of scaffold 33 of about 33 kb (referred to as L segment), and
(ii) 3' terminus of scaffold 33 of about 171 kb (referred to as 33(3') segment);
scaffold M comprises:
(i) D segment comprising:
3' terminus of scaffold 28 of about 37 kb in length (referred to as 28(3') fragment),
entire scaffold 27 of about 427 kp in length, and
5' terminus of scaffold 36 of about 52 kb in length (referred to as 36(5') fragment), and
(ii) a non-D segment comprising:
3' terminus of scaffold 36 of about 83 kb in length (referred to as 36(3') fragment), and
5' terminus of scaffold 28 of about 370 kb in length (referred to as "28(5') fragment");
scaffold F comprises:
(i) the D segment and
(ii) the 33(3') segment; and
scaffold X comprises:
(i) the L segment and
(ii) the non-D segment.

Table 1 shows the genomic characteristics of the first strain and the second strain according to certain embodiments of the present invention.

TABLE 1

| Strain to be selected | Genomic characteristics |
|---|---|
| A first strain (scaffold 33 + scaffold M) | |
| scaffold 33 (about 204 kb) L | (i) 5' terminus of scaffold 33 of about 33 kb (referred to as L segment) 1 to 33249 bp of scaffold 33 (L segment)* |
| 33(3') | (ii) 3' terminus of scaffold 33 of about 171 kb (referred to as 33(3') segment) 33250 to 204462 bp of scaffold 33 (33(3')segment)* |
| scaffold M (about 970 kb) | |
| D segment 28(3') + 27 + 36(5') | (i) D segment: (1) 3' terminus of scaffold 28 of about 37 kb in length (referred to as 28(3') fragment) 407093 to 369777 bp of scaffold 28* (2) entire scaffold 27 of about 427 kp in length 3508 to 431406 bp of scaffold 27* (3) 5' terminus of scaffold 36 of about 52 kb in length (referred to as 36(5') fragment) 1943 to 54320 bp of scaffold 36* |
| non-D segment 36(3') + 28(3') | (ii) a non-D segment: (1) 3' terminus of scaffold 36 of about 83 kb in length (referred to as 36(3') fragment) 54321-136885 bp of scaffold 36* (2) 5' terminus of scaffold 28 of about 370 kb in length (referred to as "28(5') fragment") 369776 to 1 bp of scaffold 28* |
| A second strain (scaffold F + scaffold X) | |
| scaffold F (about 680 kb) D + 33(3') | (i) D segment and (ii) the 3' terminus of scaffold 33(3') |
| scaffold X (about 480 kb) L + non-D segment | (i) the L segment and (ii) the non-D segment. |

*These nucleotides sequences of these four scaffolds (M, 33, X, F) are available online: http://bc.imb.sinica.edu.tw/~1ab229/Text_file_T1-4.rar.

A variety of methods that can be used to determine the genomic characteristics of a *T. reesei* strain as described herein are available in this art. In particular, such methods can utilize one or more oligonucleotide probes or primers including, for example, a primer set for polymerase chain reaction (PCR) that specifically hybridizes to a target region of the scaffold sequence. For example, (1) a first primer set (primer C and primer B) can be designed to target the bridge region between the L segment and the 3' terminus of scaffold 33 to determine the presence of scaffold 33; (2) a second primer set (primer A and primer D) can be designed to target the bridge region between D segment and non-D segment (i.e. crossing the break site, scaffold 36: 54323-54324) to determine the presence of scaffold M; (3) a third primer set (primer A and primer B) can be designed to target the bridge region between D segment and the 3'terminus of scaffold 33 to determine the presence of scaffold F; and (4) a fourth primer set (primer C and primer D) can be designed to target the bridge region between L segment and the non-D segment to determine the presence of scaffold X. See FIG. 8A showing the location of PCR primers A, B, C and D used for the genotyping scaffold. Tables 2-3 show certain sequences as examples of primers A, B, C and D.

TABLE 2

| Primer | Sequence | Corresponding site of scaffold |
|---|---|---|
| A | 5'-CTTCCAGCCTAAGTACTC-3' (SEQ ID NO: 1) | 54048-54065 by of Scaffold 36 |
| B | 5'-GTCGATCGTGCTAATGAAG-3' (SEQ ID NO: 2) | 33465-33438 by of Scaffold 33 |
| C | 5'-CAAGGCTATTATCCGCAG-3' (SEQ ID NO: 3) | 32892-32909 by of Scaffold 33 |
| D | 5'-CTCTGAGGGGATTAGAAG-3' (SEQ ID NO: 4) | 54498-54514 by of Scaffold 36 |

TABLE 3

Nucleotide fragments amplified bp primer sets

| Primer sets | Scaffold to be detected | Amplified fragment |
|---|---|---|
| (1) A first primer set Primer C + Primer B | Scaffold 33 | 547 bp (SEQ ID NO: 5) |
| (2) A second primer set Primer A + Primer D | Scaffold M | 467 bp (SEQ ID NO: 6) |
| (3) A third primer set Primer A + Primer B | Scaffold F | 462 bp (SEQ ID NO: 7) |
| (4) A fourth primer set Primer C + Primer D | Scaffold X | 552 bp (SEQ ID NO: 8) |

According to the present invention, the first strain and the second strain are mating competent and can mate with each other, i.e. one being a mating type and the other being the opposite mating type. In one embodiment, the first strain has a MAT1-1 locus and the second strain has a MAT1-2 locus. In another embodiment, the first strain has a MAT1-2 locus and the second strain has a MAT1-1 locus.

Once a first mating competent strain (containing scaffold 33 and scaffold M) and a second competent strain (containing scaffold F and scaffold X) are identified and chosen, they are sexually crossed. Sexual crossing of the *T. reesei* strains can be set up using conventional procedures. In particular, agar plates containing suitable types of medium can be used, e.g. malt extract agar (MEA). To carry out sexual crossing, the first strain and the second strain are inoculated on the agar plates at a proper distance from each other. The favorable conditions for induction of sexual cultures are 25° C. under either constant darkness for 2-3 weeks or under a 12h photoperiod (12h light/dark cycle) for 8-10 days. After incubation, the plates are examined for sexual structure formation. The sexual structures (stromata or fruiting bodies) are taken from the plates and washed in sterile water. Subsequently, they are cut open and ascospores thus released are grown on individual malt-extract agar (MEA) plate to determine spore viability. Each viable colony from one ascospore is isolated and transferred to a potato dextrose agar (PDA) plate. Their features, including colony morphology, colony color, genotype and/or genome-wide gene copy number, can be assessed.

Next, of the viable ascospores from the sexual crossing, a segmental aneuploidy progeny that has duplication of D segment in its genome is selected. The D segment is a nucleotide fragment of around 0.5 Mbp, comprising from 5' to 3': 3' terminus of scaffold 28 of about 37 kb in length, entire scaffold 27 of about 427 kp in length and 5' terminus of scaffold 36 of about 52 kb in length. The D segment can be confirmed by aCGH technology or Southern blot analysis.

According to the invention, the *T. reesei* SAN progeny having duplication of D segment exhibit a number of beneficial features, including enhanced gene expression or enzyme activities or growth advantages for biomass production.

In one embodiment, the *T. reesei* SAN progeny having duplication of D segment produced by the method of the invention exhibits enhanced gene expression of one or more genes encoding a carbohydrate-active enzyme (CAZyme), not only those located in the D segment but also those not located in the D segment.

Specifically, the CAZyme-encoding gene is selected from the group consisting of an endo-β-1,4-xylanase gene (xyn2; ID: 123818) at scaffold 27, a β-mannosidase gene (ID: 69245) at scaffold 28, a α-L-arabinofuranosidase gene (GH54, ID: 55319) at scaffold 2, a GH71 α-1,3-L-glucanase gene (GH71, ID: 120873) at scaffold 5, and a β-1,3-L-glucanase gene (cel3d, GH3, ID:46816) at scaffold 5.

In a certain example, the *T. reesei* SAN progeny of the invention exhibits enhanced xylanase activities.

In another embodiment, the *T. reesei* SAN progeny of the invention produces increased biomass on a xylan-based medium.

As used herein, when describing one or more beneficial features of the *T. reesei* SAN progeny of the invention, the term "enhanced", "increased" or "higher" is used interchangeable to compare such beneficial features of the *T. reesei* SAN progeny of the invention with the corresponding features of a control *T. reesei* strain, e.g. a parent strain or a euploid progeny strain, which does not have duplication of D segment. For example, an "enhanced" level of gene expression of one or more genes, an "increased" level of enzyme activities, or a "higher" level of biomass production of the *T. reesei* SAN progeny of the invention, means that the level is increased 20% or more, 30% or more, 50% or more, 75% or more, 100% or more, 2 fold or more, 3 fold or more, 5 fold or more, or 10 fold or more relative to a control strain, e.g. a parent strain or a euploid progeny strain, which does not have duplication of D segment. The increase or enhancement can be determined by methods with which the skilled persons are familiar. Examples of such methods include but are not limited to protein assay, Northern or Southern hybridization, reverse transcription (quantitative RT-PCR), ELISA (enzyme-linked immunosorbent assay), Western blotting, or radioimmunoassay (RIA). In some embodiments, the method of the invention may further comprise (e) selecting a SAN progeny with duplication of D segment which has one or more beneficial features as described herein.

In our study, it is further found that loss of a non-homologous end joining (NHEJ) gene can stabilize segmental duplication i.e. prevent a SAN progeny of the invention returning to euploid.

In particular, the present invention provides a method of producing a stable, SAN strain of *T. reesei*, comprising:
(a) sexually crossing two haploid mating competent strains of T. with chromosome heterozygosity, wherein at least one of the parent strains includes deletion of a NHEJ gene; and
(b) identifying and selecting a resultant SAN progeny of *T. reesei* from step (a) that has deletion of the NHEJ gene.

The term "non-homologous end-joining" refers to a natural, cellular process in which a double-stranded DNA-break is repaired by the direct joining of two non-homologous DNA segments. *T. reesei* NHEJ genes that encode Ku70, Ku80 and Lig4 were previously referred to as tku70, tku80 and tmus53, respectively Ku70 and Ku80, form a heterodimer and function as a molecular scaffold at DSB ends to which other NHEJ proteins (e.g., the DNA ligase IV, Lig4) can bind to.

According to the present invention, a NHEJ gene can be removed from either or both of the parent stains, before sexual crossing, such that a SAN progeny after sexual crossing between these two parent strains, having deletion of the NHEJ gene, can be produced and selected. In some embodiments, a NHEJ gene as used herein is tku70 or tmus53. Gene deletion can be performed via methods known in the art [16, 17].

According to the invention, a SAN progeny with deletion of a NHEJ gene can stabilize segmental duplication for an extended period of time e.g. 2 weeks or more, 3 weeks or more, 4 weeks or more, 5 weeks or more, 6 weeks or more, or 7 weeks or more.

In certain embodiments, a first mating competent strain (scaffold 33 and scaffold M) and a second mating competent strain (scaffold F and scaffold X), at least one of which has deletion of a NHEJ gene are provided, then sexual crossing is carried out between these two strains, and a resultant progeny having duplication of D segment and deletion of the NHEJ gene is identified and selected.

Specifically, a SAN progeny having duplication of D segment and deletion of the NHEJ gene according to the present invention exhibits superior features, not only generating more biomass but also exhibiting higher production of hemicellulose for an extended period of time (e.g. more than 7 weeks, 50 days). See FIG. 11B and FIG. 11D.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

We report that the 16 part-ascospores are generated via meiosis and two rounds of postmeiotic mitosis. Notably, the CBS999.97(1-1) haploid genome, compared to those of CBS999.97(1-2) and QM6a(1-2), comprises segmental rearrangements in two genomic scaffolds. Due to sequence heterozygosity, most 16-ascospore asci (>90%) contain 4 or 8 inviable ascospores with an equal number of viable segmentally aneuploid ascospores. Duplication of a ~0.5 Mbp chromosomal segment enhances production of hemicellulases. Further, remarkably, deletion of the nonhomologous end-joining (NHEJ) gene (tku70 or ligase IV tmus53) can stabilize segmental duplication, indicating that NHEJ but not homologous recombination is responsible for the restoration of euploidy. We have applied our findings to generate mutants that produce more hemicellulases than RUT-C30, a widely used industrial strain for lignocellulosic biomass degradation.

1. Materials and Methods
1.1 Strains and Sexual Crossing

*H. jecorina* CBS999.97 wild isolate haploid strains [5,15], the tku70Δ QM6a mutant [16] and the tmus53Δ QM6a mutant [17] have been described previously. The two CBS999.97 haploid mutants were generated by crossing each QM6a mutant with the wild isolate CBS999.97(1-1), respectively. The corresponding offspring mutants were backcrossed at least twice with the CBS999.97(1-1) or CBS999.97(1-2) strains. Sexual crossing was carried out as described previously [5,15].

*T. reesei* sexual crossing was performed as previously described [15]. In brief, CBS999.97(1-1) was crossed with CBS999.97(1-2) or QM6a on a 10-cm malt extract agar (MEA) plate. The MEA plate was incubated at 25° C. under either constant darkness for 2-3 weeks or under a 12h photoperiod (12h light/dark cycle) for 8-10 days. A plant growth chamber with a light intensity of about 80 μmol/m$^2$/s was used in this study.

1.2 Hexadecad Dissection

For ascospore (or the sexual spore) isolation, mature hexadecads were manually isolated from stomata and transferred onto the center of a 10-cm malt extract agar (MEA) plate. Yeast tetrad dissection using a micromanipulator was applied to sequentially separate and isolate each ascospore in a hexadecad. The fiberglass needle could readily break the fragile ascus wall and separate each ascospore, leaving the remaining part intact. After incubation in a plant growth at 25° C., each viable ascopsore germinated to form a mycelium colony. Each mycelium colony was transferred to a potato dextrose agar (PDA) plate to determine colony morphology and colony color, and then characterized by genotyping and aCGH analysis.

1.3 Deep Sequencing and De Novo Assembly of the Wild-Type CBS999.97(1-2) Genome

The shotgun library for 454 Sequencing was prepared with 0.5 μg of genomic DNA from wild isolate CBS999.97 (1-2) haploid using the GS Rapid Library Prep Kit following the manufacturer's protocol (Roche 454; 454 Life Sciences, Connecticut, USA). The resulting library was examined by the BioAnalyzer DNA Chip assay (Agilent Technologies; California, USA), and FAM fluorescence was quantified using a Modulus fluorometer (Turner Biosystems; California, USA). Sequencing was performed on a GS FLX Titanium system in the High Throughput Sequencing Core Facility at the Biodiversity Research Center at Academia Sinica, Taiwan. Raw reads were obtained from 2.5 sequencing runs totaling 873 Mb, with median read lengths ranging from 351 to 454 nt among the five datasets. De novo assembly was performed using Newbler v.2.5.3 (Roche 454) on a single CPU. The draft genome assembly consisted of 1,087 contigs with sizes ranging from 500 bp to 404,555 bp, with an average contig and N50 size of 29,833 bp and 66,873 bp, respectively. Additional de novo assembly and gene annotation were conducted by an in-house computational core. The assembled CBS999.97(1-2) genomic sequences are available online (http://140.109.32.39/~lab229/contig_info/index.php).

For evaluation of the deep sequencing results, the community annotation including the Gene Ontology (GO) classification is available from the *T. reesei* genome database v.2.0 (http://genomejgi-psf.org/Trire2/Trire2.home.html). Annotation was performed using BLAST to search for orthologous genes of *Trichoderma reesei* v.2.0 and *Trichoderma virens* Gv29-8 v2.0. Gene sequences were downloaded from the Joint Genome Institute (JGI) database (http://genomejgi-psf.org/); there are 9,143 genes in QM6a and 12,427 in *T. virens*. We identified 8,106 CBS999.97(1-2) and QM6a orthologous genes with high sequence similarity (≥90%). Of the remaining genes (similarity <90%), we found 49 that existed only in QM6a, without any similarity to genes in the CBS999.97(1-2) genome.

1.4 Array-Based Comparative Genomic Hybridization (aCGH) and Data Analysis

Genomic DNA was isolated using standard techniques and fragmented by a Bioruptor Sonicator (Diagenode, UCD-200) using repeated cycles of 75 seconds on (high) and then 75 seconds off for a total of 15 minutes, producing a median DNA size of 500 bp (range 200-1000 bp). The fragmented DNA was then quantified using a NanoDrop ND-1000 UV-VIS Spectrophotometer to assess the gDNA concentration and purity. Fragmented genomic DNA samples were labeled with Cy5 or Cy3 using a NimbleGen dual-color DNA labeling kit (Roche NimbleGen, Madison, Wis.). Test sample genomic DNA was end-labeled with Cy3, whereas CBS999.97(1-1) or QM6(1-2) genomic DNA was labeled with Cy5 and used as a reference to measure DNA copy number changes. The Cy5- and Cy3-labeled genomic DNA samples were hybridized to custom-designed oligonucleotide arrays (4×72000 formation) by Roche-NimbleGen based on the CBS999.97(1-2) genome sequence and *T. reesei* v2.0 genome sequence, respectively [15,18].

DNA end-labeling, hybridization, and scanning were performed by the Academia Sinica Institute of Molecular Biology Microarray Core using the NimbleGen Systems technique (NG_CGH&CNV_Guide_v7p0), following the vendor's standard operating protocol. Image data were processed using NimbleScan software version 2.6.3 (Roche NimbleGen) to obtain the raw intensity data (.pair file). Data analysis and normalization were performed using Agilent GeneSpring GX 11.5.1 by an in-house bioinformatics core. Raw intensity scales were transformed by quantile normalization which was used to correct array biases and makes all distributions uniform. We found that the aCGH results of QM6a microarrays were consistent with those of CBS999.97 microarrays, and the latter were submitted to the Gene Expression Omnibus (GEO).

1.5 Genome-Wide Microarray Hybridization

Total RNA isolation and genome-wide mRNA microarray experiments have been described recently [15]. All experiments were conducted in technical triplicates with at least three different biological replicates. Data analysis and normalization were performed using Agilent GeneSpring GX 12.0. Raw intensity scales were transformed by quantile normalization, which was used to correct array biases and to make all distributions uniform. Both t-test and fold change criteria were employed simultaneously to identify differentially expressed genes with P value 0.05 and fold change ≥1.5. In the strain cluster analysis, hierarchical method is used for the clustering algorithm and Euclidean distance method is used in the similarity measurement.

1.6 Shake Flask Cultures

Conidia from three-day old plates (10 cm diameter dishes) were harvested with 1 mL of sterile spore solution [0.8% NaCl, 0.05% Tween 20 (Sigma)], vortexed and filtered through glass wool. The volume was then adjusted to $OD_{600nm}$ of 0.3, and 1 mL of the spore suspension was transferred to 250 ml Erlenmeyer flasks containing 50 ml of Mandels-Andreotti basal medium prepared in 0.1 M citrate-phosphate buffer (pH 5.0) and supplemented with 1 g $L^{-1}$ peptone and 0.33 g $L^{-1}$ urea. As a carbon source, 10 g $L^{-1}$ Solka floc 200 (International Fiber Corporation, North Tonawanda, USA) or birchwood xylan (Sigma Aldrich, USA) was added to induce cellulase or xylanase expression, respectively. After 3 days of cultivation in constant darkness at 25° C. on a rotary shaker (200 rpm) flasks were used for biomass determination and enzymatic assays.

1.7 Biomass Determination

For biomass determination 50 mL shake flask culture was filtered onto a dry Miracloth (Calbiochem, Darmstadt, Germany), washed with distilled water, and dried with paper towels. The fungal mycelia were collected, frozen with liquid nitrogen, and stored at −80° C. until use. For total protein quantification, the fungal sample was dissolved in 5 mL of 0.1 N NaOH. The solution was sonicated by a digital sonifier (Branson) at a duty cycle setting of 30% for 6 minutes total with 30 seconds on and 30 seconds off. The sample was then incubated at room temperature for 3 h and centrifuged at 5251× g for 10 min The protein concentration of the supernatant was determined by modified Lowry protein assay, using bovine serum albumin as a standard.

1.8 Enzymatic Assays

For endo-1,4-β-glucanase (cellulase) activity measurements, supernatant diluted from 1:2 to 1:10 was added to an Azo-CM-cellulose solution (S-ACMCL; Megazyme International, Ireland). The procedure was carried out according to the manufacturer's instructions. Azo-CM-cellulose is a dyed polysaccharide with Remazol Brilliant Blue R at a concentration of approximately one dye molecule per 20 sugar residues (Megazyme International). This assay is much more sensitive (50-100 fold) than the filter paper assays (e.g., DNS method).

To measure endo-1,4-β-D-xylanase (xylanase) activity, supernatant diluted from 1:2 to 1:10 was prewarmed at 40° C. for 5 minutes. A xylazyme AX test tablet substrate (T-XAX200; Megazyme International) was added to the supernatant (0.5 mL) and incubated at 40° C. for 10 minutes. The reaction was stopped by adding 10 ml stop solution (2% Trizma Base, pH ~9). The sample was centrifuged at 2000× g for 10 min, and absorbance was measured at 590 nm *Aspergillus niger* xylanase (~300 mU/mL) was used as a control following the procedure specified by the manufacturer.

Figure 1:
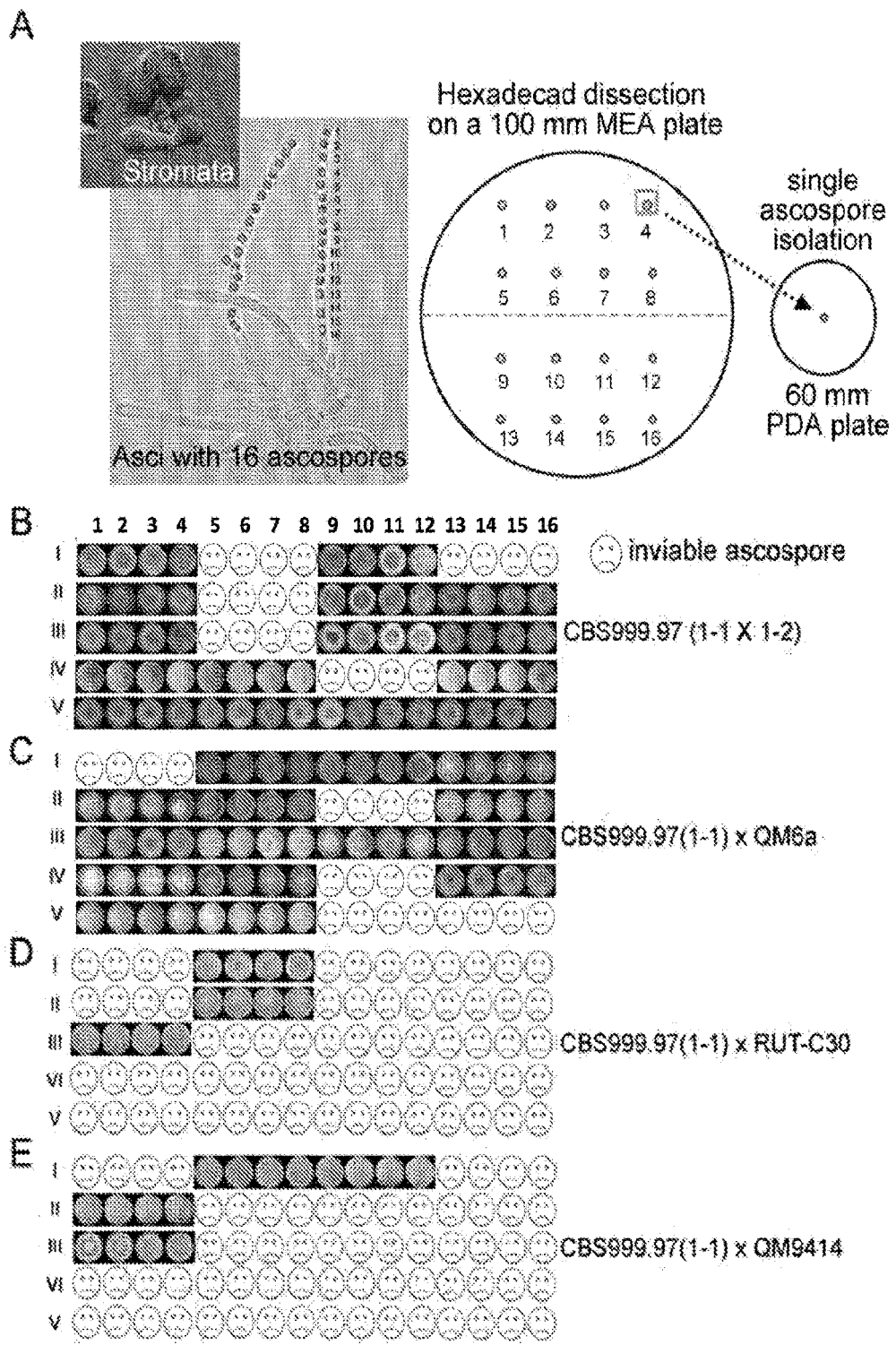
FIG. 1 shows the hexadecad dissection and its results. (A) Upper panel, stroma; lower panel, developing asci of which two contain 16 ascospores. Each ascospore is numbered according to its order in the ascus. Sixteen ascospores from a hexadecad were sequentially separated and grown on individual 100-mm malt-extract agar (MEA) plates. A single colony from one ascospore was isolated and transferred individually to a 60-mm potato dextrose agar (PDA) plate. (B) Sexual crossing of the wild isolate CBS999.97(1-1) with CBS999.97(1-2) (n≥20), QM6a (n≥10), RUT-C30 (n≥10) or QM9414 (n≥10) to generate hexadecads in constant darkness. Sixteen wild ascospores generated in constant dark. Sixteen single-ascospore colonies were aligned sequentially according to the ascospore order. Inviable ascospores are indicated by a sad face symbol.
Figure 2:
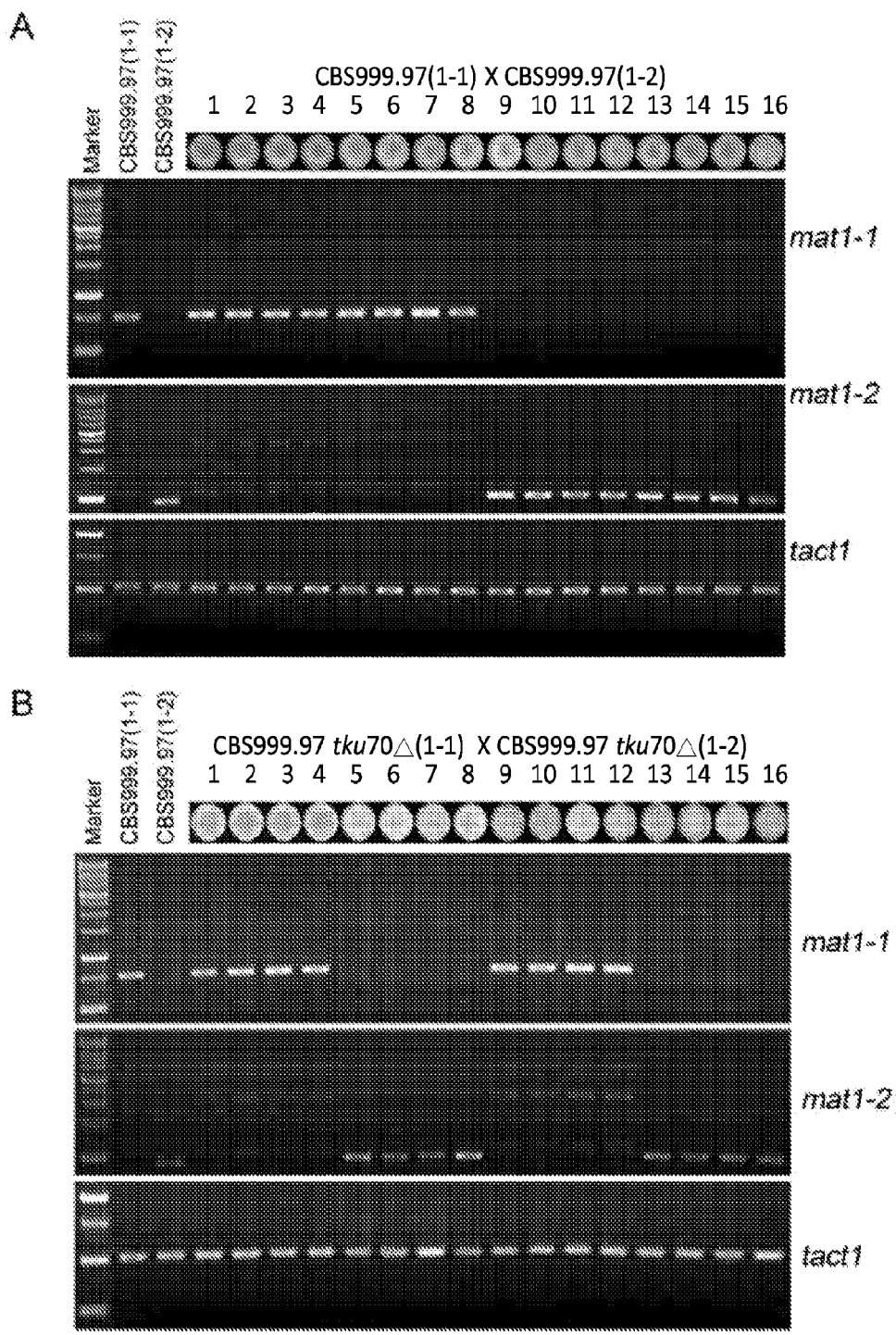
FIG. 2 shows the results of genotyping. Genomic PCR analysis of mat1-1, mat1-2 and tact1 (actin) genes in all sixteen viable ascospores generated by the CBS999.97 wild isolate diploid and a tku70Δ diploid. The parental wild isolate haploid strains, CBS999.97(1-1) and CBS999.97(1-2), were used as controls.
Figure 3:
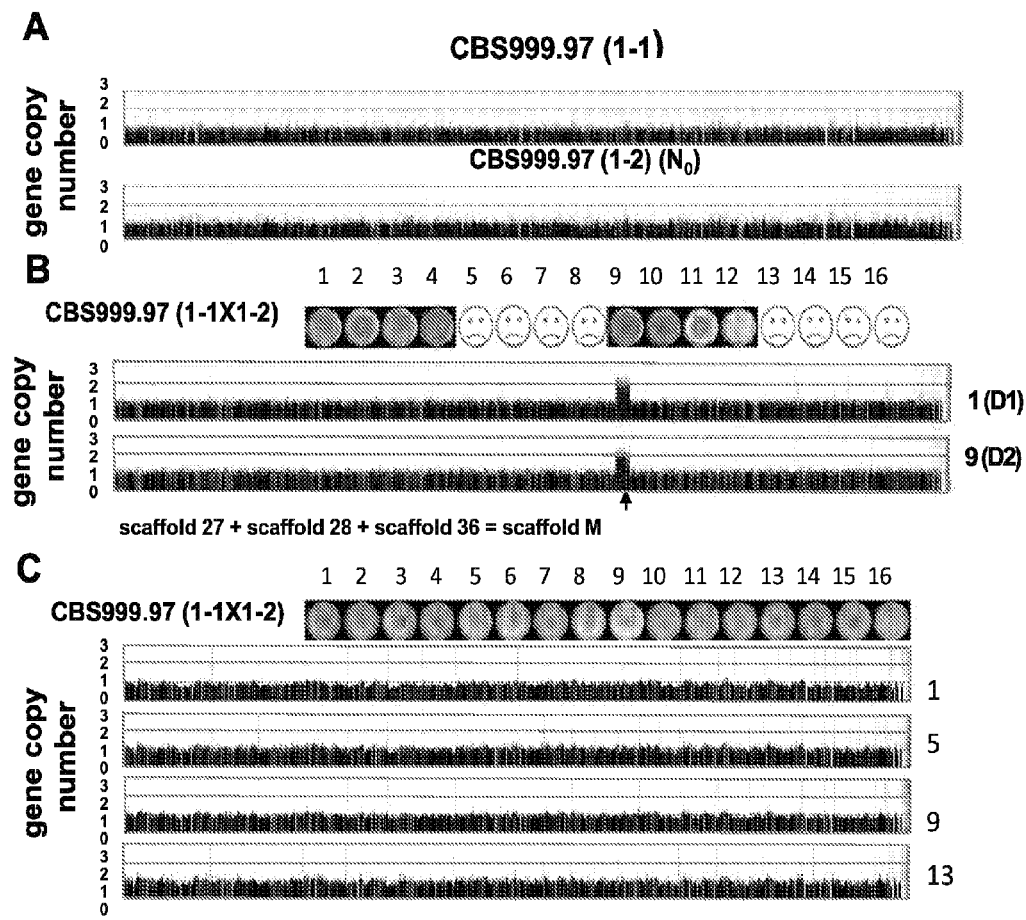
FIG. 3 shows the results of array-based comparative genomic hybridization (aCGH). CBS999.97(1-1) genomic DNA was used as a reference to measure DNA copy number changes. Each line in the histogram represents one oligonucleotide and its position in the QM6a and CBS999.97(1-2) genome sequence. The QM6a genome assembly comprises 89 scaffolds. Three contiguous scaffolds (27, 28, 36) were reassembled into a much larger scaffold M. Normalized means for the oligonucleotides covering the 87 scaffolds are shown. The 87 scaffolds are ordered from left to right according to their length. The length of scaffold M is slightly shorter than that of scaffold 11. Gene copy number of the two parental wild isolate haploids (A) and the representative ascospore colonies of the wild isolates (B-F) are shown on the left. The data is available at Gene Expression Omnibus accession number GSE-40850. The five strains with duplicated segments (D1-D5) and the seven euploid control strains (N0-N6) are also indicated.
Figure 3:
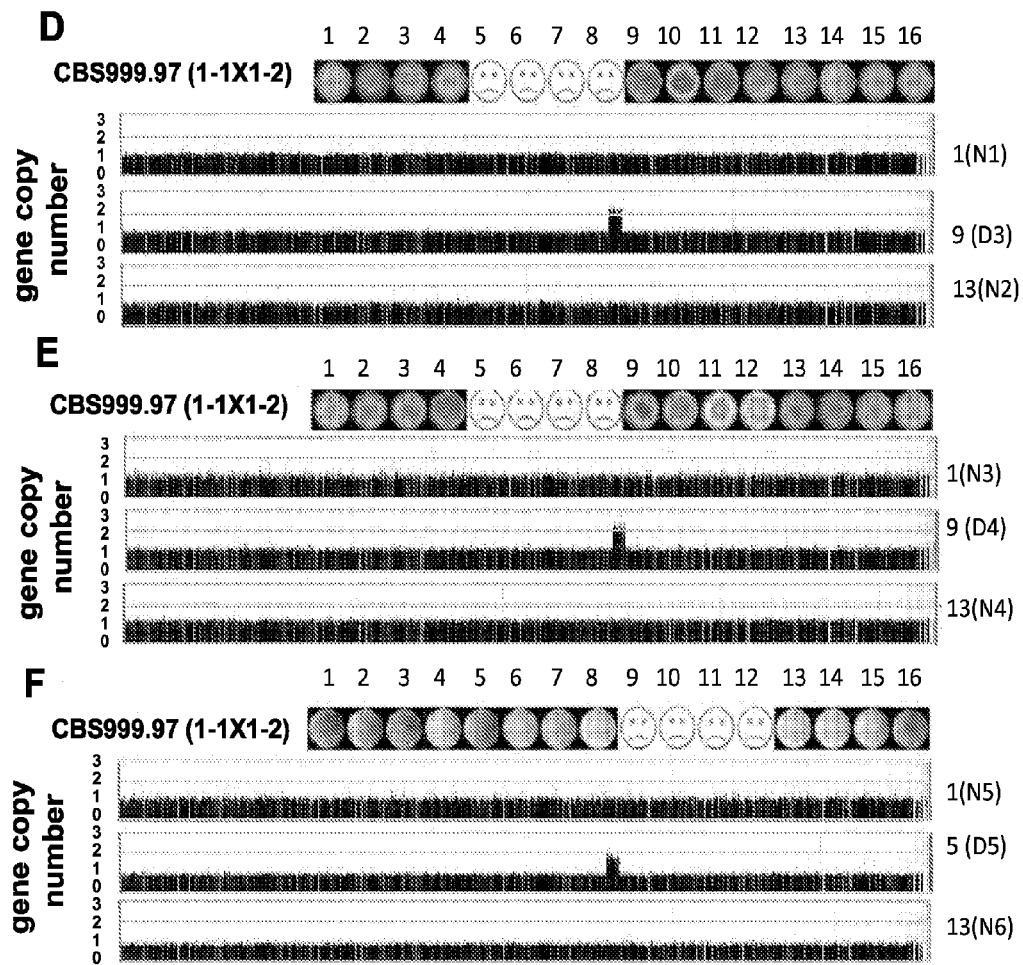

2. Results 2.1 In *T. reesei* each of the Four Meiotic Products Undergoes Two Further Mitotic Divisions We applied yeast tetrad dissection to sequentially separate the 16 ascospores from an ascus on an agar plate. Each ascospore was numbered according to its linear order in the ascus and then cultured at 25° C. in darkness for 2 days to determine spore viability. To prevent cross contamination, each viable colony was transferred individually to another plate (FIG. 1A). The 16 ascospores were compared and classified based on viability, colony morphology, colony color (FIG. 1B-1E), PCR genotyping (FIG. 2) and aCGH with NimbleGen microarrays [15,18] (FIG. 3). Primers used for genomic PCR are as follows:

TABLE 4

| Protein ID or location | Gene names | Primer | Nucleotide sequence |
|---|---|---|---|
| 44504 | tact1 | Forward | 5' ATGATCGGTATGGGTCAG 3' (SEQ ID NO: 14) |
| | | Reverse | 5' GATGTCACGGACGATTTC 3' (SEQ ID NO: 15) |
| Genebank accession number FJ599756 | mat1-1 | Forward | 5' AGCCGAGATACCTCAATG 3' (SEQ ID NO: 16) |
| | | Reverse | 5' ACCTGTCCTCCAATCTTC 3' (SEQ ID NO: 17) |
| 124341 | mat1-2 | Forward | 5' TCAGTCAACGCAGTCATG 3' (SEQ ID NO: 18) |
| | | Reverse | 5' CATTGGCACAAGCGAC 3' (SEQ ID NO: 19) |
| 63200 | tku70 | Forward | 5' CAGGAGACTCCAAGTTTGATC 3' (SEQ ID NO: 20) |
| | | Reverse | 5' TGCTGCGCTTCTTGAATC 3' (SEQ ID NO: 21) |
| 58509 | tmus53 | Forward | 5' GAGATAGGTGTAGTCCTTGG 3' (SEQ ID NO: 22) |
| | | Reverse | 5' GAGAAGACGTTCCTATACCT 3' (SEQ ID NO: 23) |

Figure 4:
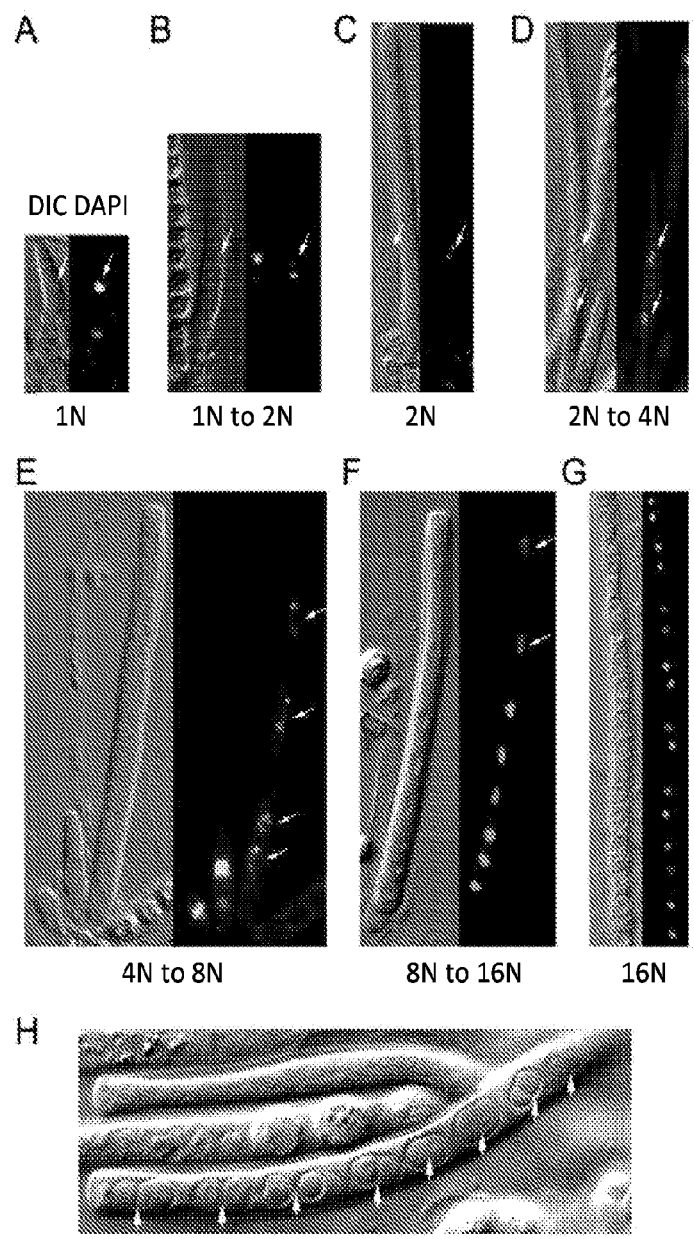
FIG. 4 shows visualization of four rounds of nuclear divisions during H. jecorina ascospore formation/maturation. (A-G) Developing asci were manually dissected, stained with DAPI, and then visualized by fluorescent microscopy. DIC and DAPI fluorescent images are shown. Nuclei (N) are marked by white arrows. (H) A DIC image of developing asci showing synchronous division of 8 nuclei (8N) into 16 nuclei (16N).

The 16 ascospores from each hexadecad could be readily classified into four linearly arranged groups, and each group contained 4 genetically identical ascospores. These findings revealed that the 16 ascospores are generated via meiosis followed by two rounds of postmeiotic mitosis. By staining the developing asci with 4', 6-diamidino-2-phenylindole (DAPI), we also visualized the two meiotic divisions and the two further mitotic divisions using a fluorescent microscopy (FIG. 4).

2.2 Induction of Segmental Aneuploidy in Meiosis

We found that sexual crossing of CBS999.97(1-1) with CBS999.97(1-2) (FIG. 1B) or QM6a(1-2) (FIG. 1C) produced high rates of inviable ascospores. The majority of the hexadecads (>90%, n≥30) contained either 8 or 12 viable ascospores. The two cellulase-overproducing mutants, RUT-C30 (FIG. 1D) and QM9414 (FIG. 1E), also could mate with CBS999.97(1-1) but often generated hexadecads with 0 or 4 viable ascospores.

Figure 5:
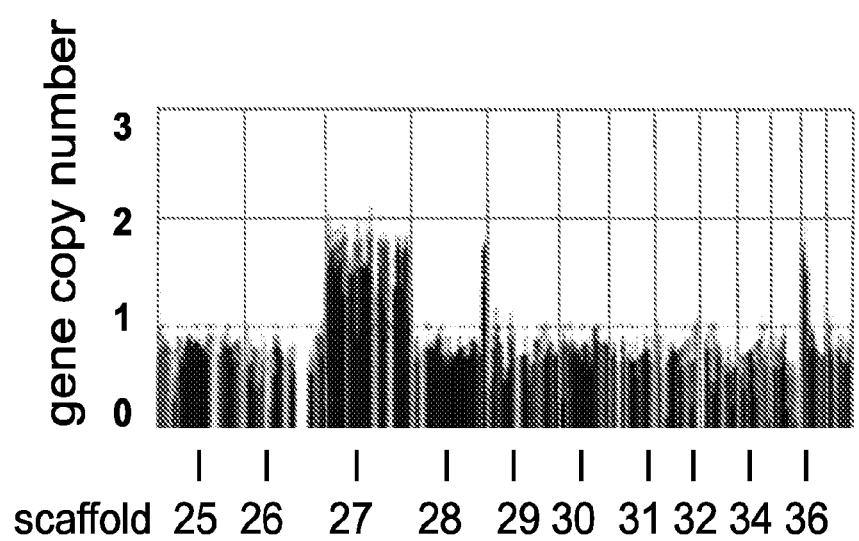
FIG. 5 shows a representative array-based comparative genomic hybridization (aCGH) result of viable segmentally aneuploidy (SAN) progeny. Normalized means for the oligonucleotides covering the scaffolds 25-37 are shown. These scaffolds are ordered from left to right according to their length.

QM6a has seven chromosomes and its genome is 34.1 Mb in size. The *T. reesei* v2.0 QM6a genome database (Joint Genome Institute, USA) comprises 89 scaffolds and 97 contigs [1]. We applied the aCGH technique to identify genome-wide gene copy number. The aCGH results revealed that the two CBS999.97 parental haploid strains are euploid (FIG. 3A). In contrast, all viable progeny generated from 8 viable ascospore hexadecads (FIG. 3B) had a copy gain within the entire scaffold 27 (134 genes and ~424 kb), the 3' terminus of scaffold 28 (12 genes, ~31 kb), and the 5' terminus of scaffold 36 (15 genes, ~54 kp) (FIG. 5). By deep-sequencing the CBS999.97(1-2) genome, we found that the duplicated regions (referred to as "D segment" as shown in FIG. 6 and FIG. 7) in these three scaffolds (27, 28 and 36) are contiguous segments. These three scaffolds were then reassembled into a much longer scaffold, which is referred to as scaffold "M" (FIG. 3B, FIG. 6 and FIG. 7). Genomic PCR, sequencing and Southern blotting analyses further revealed that scaffold M is located near a telomere, because the 3' terminus of scaffold M is connected to a repeated hexanucleotide sequence, TTAGGG, which is the telomeric repeat of QM6a [1]. We also showed that all ascospores in a hexadecad with 16 viable ascospores were euploid and thus without the D segment duplicated (FIG. 3C). By contrast, in wild-type CBS999.97 hexadecads with 12 viable ascospores, there were 8 euploid ascospores and 4 SAN ascospores with the D segment duplicated (FIG. 3D-3F).

Figure 8:
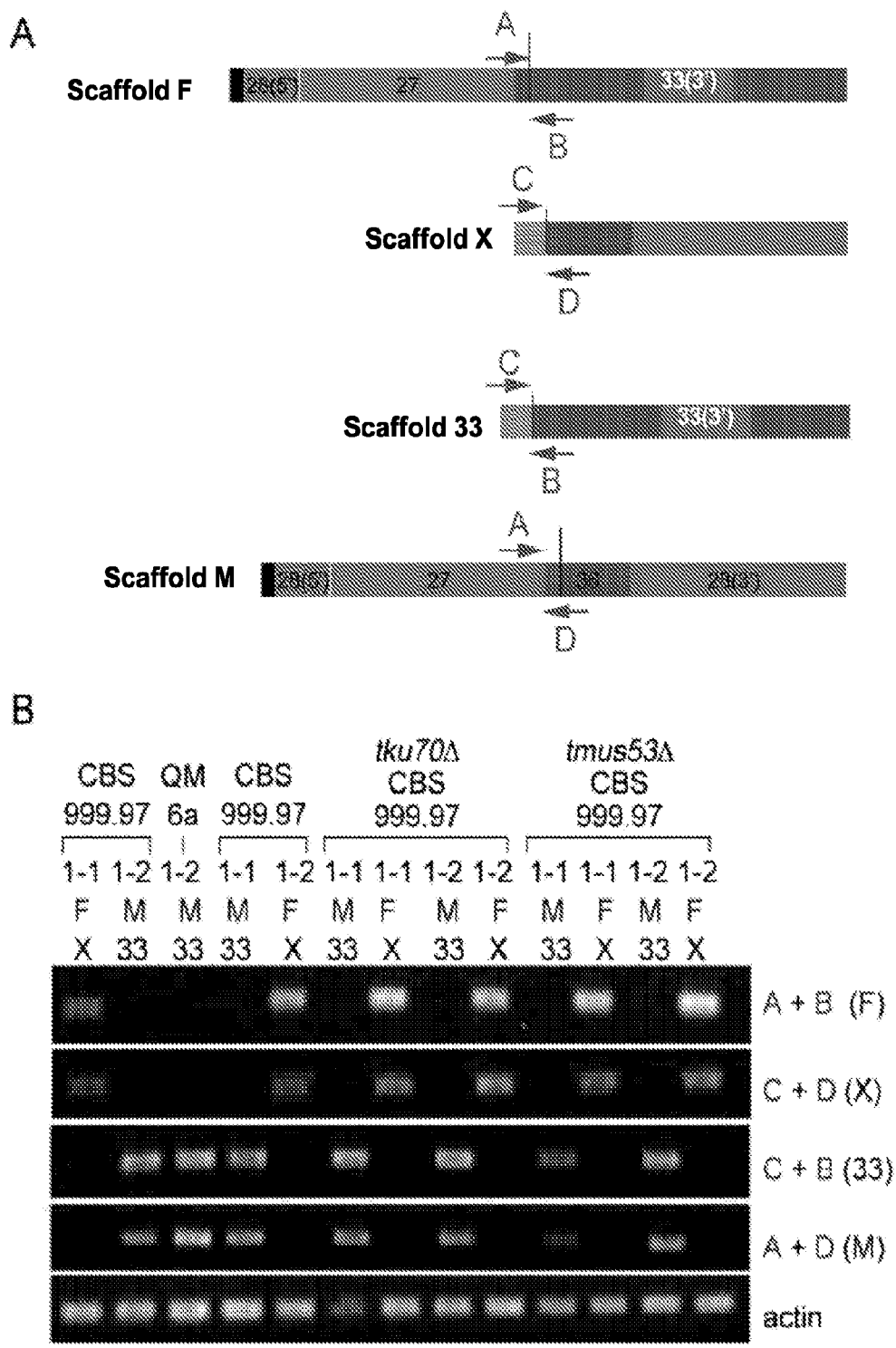
FIG. 8 shows that chromosome heterozygosity, but not NHEJ, is responsible for the formation of segmental aneuploid progeny in meiosis.

The aCGH results further revealed that the putative DNA double strand break site (scaffold 36:54323-54324 bp) responsible for segmental duplication resides within the second intron of a novel gene (ID 112288). Additional PCR and sequencing analyses revealed that the first exon (scaffold 36:53664-53943 bp) of this novel QM6a gene is deleted in both haploid genomes of the wild isolate CBS999.97 (FIG. 7). Notably, compared to the wild isolate CBS999.97 (1-2) and QM6a genomes, the wild isolate CBS999.97(1-1) genome exhibits large segmental translocations: (1) The 5' terminus of scaffold 33 (1-33,249 bp; referred to as "L" segment) links the non-duplicated region of scaffold M to form a new scaffold "X" in CBS999.97(1-1); (2) The 3' terminus of scaffold 33 (33250-297,000 bp) and the D segment of scaffold M physically link and form a new scaffold "F" in CBS999.97(1-1) (FIG. 6 and FIG. 7). To determine whether chromosome heterozygosity is responsible for segmental duplication in meiosis, we crossed the two wild isolate haploids CBS999.97(1-1, F, X) and the CBS999.97(1-2, M, 33) to generate two new haploids CBS999.97(1-1, M, 33) and CBS999.97(1-2, F, X) (FIG. 8). The presence of these four scaffolds in these haploids was determined by diagnostic PCR using four specific primers (A-D), respectively (Table 5).

TABLE 5

| Primer name | Sequence |
|---|---|
| A | 5' CTTCCAGCCTAAGTACTC 3' |
| B | 5' GTCGATCGTGCTAATGAAG 3' |
| C | 5' CAAGGCTATTATCCGCAG 3' |
| D | 5' CTCTGAGGGGATTAGAAG 3' |

SEQ ID NOS: 1-4, respectively

We found that all the 16 ascospores generated by crossing CBS999.97 (1-1, F, X) with CBS999.97(1-2, F, X) or CBS999.97(1-1, M, 33) with CBS999.97(1-2, M, 33) were viable. Deletion of the nonhomologous end-joining (NHEJ) gene, tku70 or DNA ligase IV tmus53, did not affect meiosis, ascospore number or ascospore viability in any of the relevant strains (Table 6).

TABLE 6

Chromosome heterozygosity, but not NHEJ genes (tku70 and tmus53), is responsible for the formation of meiotic-driven SAN progeny.

| Strain background | Sexual crossing | # of asci with 4 or 8 inviable ascospores | # of asci dissected |
|---|---|---|---|
| CBS999.97 | (1-1, F, X) × (1-2, M, 33) | 19 | 20 |
| | (1-1, M, 33) × (1-2, F, X) | 0 | 10 |
| | (1-1, F, X) × (1-2, F, X) | 0 | 10 |
| CBS999.97 tku70Δ | (1-1, F, X) × (1-2, M, 33) | 8 | 10 |
| | (1-1, M, 33) × (1-2, F, X) | 0 | 10 |
| | (1-1, F, X) × (1-2, F, X) | 0 | 10 |
| CBS999.97 tmus53Δ | (1-1, F, X) × (1-2, M, 33) | 10 | 10 |
| | (1-1, M, 33) × (1-2, F, X) | 0 | 10 |
| | (1-1, F, X) × (1-2, F, X) | 0 | 10 |

Figure 9:
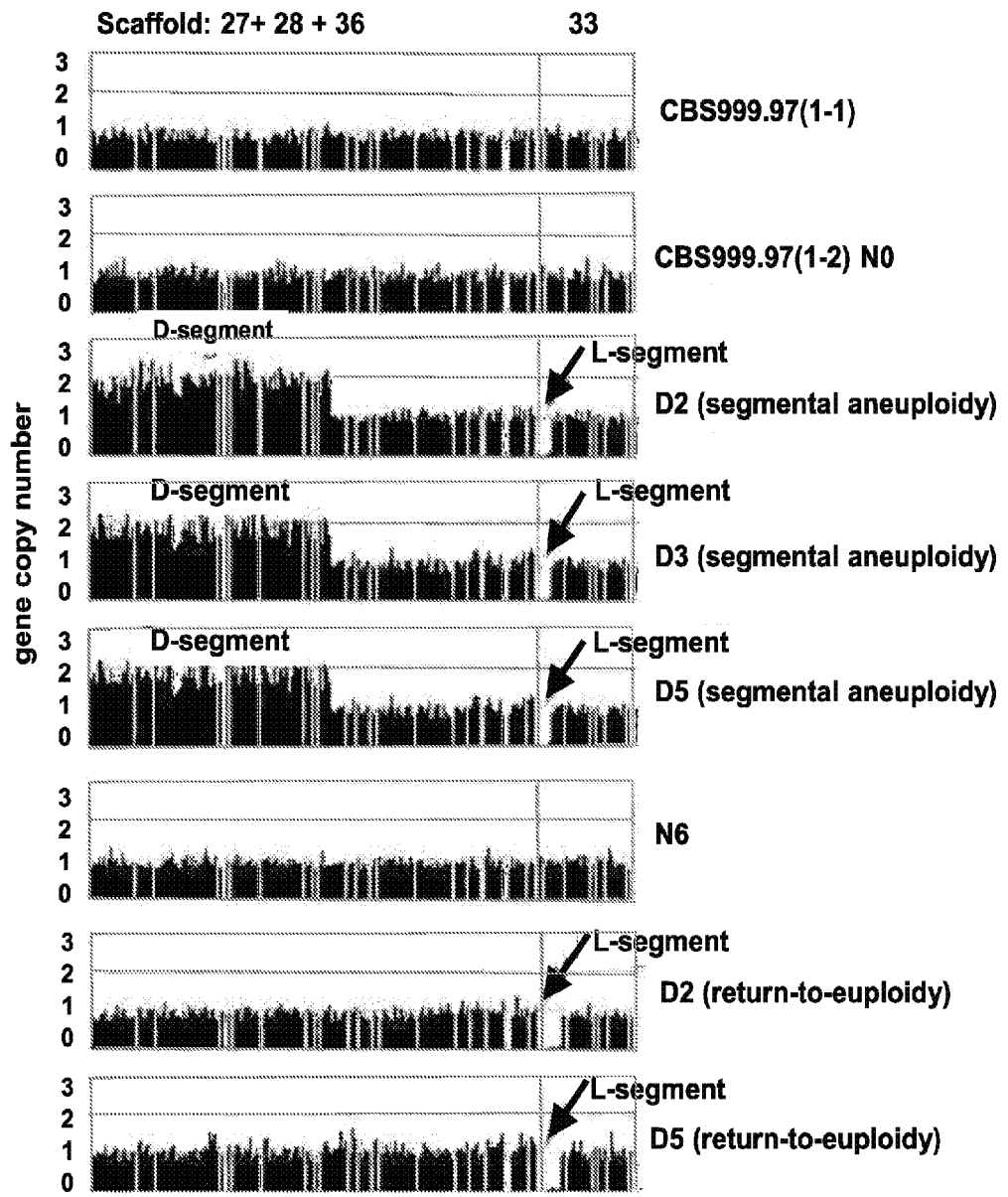

These results suggest that homologous recombination between these two pairs of homeologous scaffolds (M/F and 33/X) is responsible for the formation of SAN ascospores during meiosis. Accordingly, we propose a model (FIG. 6) describing how homologous recombination results in viable SAN ascospores with two D segments but no L segment as well as inviable ascospores with two L segments. This hypothesis is consistent with our aCGH results (FIG. 9), that all SAN ascospores (D2, D3 and D5) lack the L segment.

2.3 Southern Blot Analysis

To further confirm the presence of duplication of D segment, a Southern blot analysis was conducted.

*T. reesei* genomic DNA was digested by BsmBI, electrophoresed on an 0.8% agarose gel, analyzed by Southern blotting with a $^{32}$P-labelled DNA probe, and then visualized using a Fujifilm phosphoimager. The DNA probe (304 bp) (SEQ ID NO: 9) was amplified by PCR using two oligonucleotide primers,

```
PA7543
                                      (SEQ ID NO: 10)
(5'-AGCTACATGAGATCCTGCAT)
and PA7544
                                      (SEQ ID NO: 11)
(5'-TCAGGTGCACTCTGCACGAA).
```

TABLE 7

| Primer | Sequence | Corresponding site of scaffold |
|---|---|---|
| PA7543 | 5'-AGCTACATGAGATCCTGCAT (SEQ ID NO: 10) | Scaffold 36: 53934-53954 bp |
| A7544 | 5'-TCAGGTGCACTCTGCACGAA (SEQ ID NO: 11) | Scaffold 36: 54258-54238 bp |

Southern blot were visualized by exposure to an X-ray film (GE Healthcare, USA). The molecular weight markers were indicated on the left. The CBS999.97(1-1) parental haploid strain has a 443 bp band (SEQ ID NO: 12), whereas the CBS999(1-2) parental haploid strain has a 1512 bp band (SEQ ID NO: 13). The SAN progeny have both bands. After returning into euploidy (RTU), only the 433 bp band was loss. See FIG. 12.

2.4 The Ancestral *T. reesei* Genome Might Contain Scaffold M and
Scaffold 33

The sexually competent CBS999.97 strain was isolated from a storage lake in French Guiana [23], whereas QM6a was found on the Soloman island during the Second World War. Several other non-CBS999.97 haploid strains were isolated from different geographical locations [5]. Diagnostic PCR was applied here to study the distribution of the four scaffolds (M, 33, F, X) in 9 representative non-CBS999.97 isolates, which were isolated from French Guiana, Brazil, Indonesia and New Caledonia, respectively. Using the four primers (A-D) describe above (Table 2, Table 5 and FIG. 7), we were able to detect scaffold 33 in 8 isolates (except G.J.S 84-473) and scaffold M in 6 isolates (except G.J.S 84-473, G.J.S 86-410 and G.J.S 93-23). Intriguingly, Scaffold F and Scaffold X were not detected in all 9 non-CBS999.97 isolates (Table 8), indicating that the genomes of these non-CBS999.97 isolates might be more similar to those of QM6a and CBS999.97(1-2) than that of CBS999.97(1-1).

TABLE 8

Genomic PCR genotyping the four scaffolds (M, F, 33, X) in *T. reesei* wild isolates and industrial strains.

| Wild isolate | Origin | Mating type | PCR primers A + B (F) | PCR primers C + D (X) | PCR primers C + B (33) | PCR primers A + D (M) |
|---|---|---|---|---|---|---|
| CBS999.97 | French Guiana | MAT1-1 | + | + | − | − |
| CBS999.97 | French Guiana | MAT1-2 | − | − | + | + |
| QM6a | Solomon Islands | MAT1-2 | − | − | + | + |
| G.J.S. 86-404 | French Guiana | MAT1-1 | − | − | + | + |
| G.J.S. 86-410 | French Guiana | MAT1-1 | − | − | + | − |
| G.J.S. 84-473 | French Guiana | MAT1-1 | − | − | − | − |
| G.J.S. 89-7 | Brazil Para | MAT1-2 | − | − | + | + |
| G.J.S. 97-178 | Brazil Para | MAT1-2 | − | − | + | + |
| G.J.S. 85-249 | Indonesia Celebes | MAT1-1 | − | − | + | + |
| G.J.S. 85-229 | Indonesia Celebes | MAT1-2 | − | − | + | + |
| G.J.S. 85-236 | Indonesia Celebes | MAT1-2 | − | − | + | + |
| G.J.S. 93-23 | New Caledonia | MAT1-2 | − | − | + | − |
| QM9414 | | MAT1-2 | − | − | + | + |
| RUT-C30 | | MAT1-2 | − | − | + | + |

This hypothesis was further confirmed by sexual crossing and single ascospore isolation experiments: first, CBS999.97(1-2, M, 33) could mate with 3 French Guiana isolates (G.J.S. 86-404, 86-410 and G.J.S. 84-473) and generated asci with 16 viable ascospores, though our diagnostic PCR method failed to detect scaffold M and scaffold 33 in G.J.S. 84-473. Second, almost all asci generated by sexually crossing CBS999.97(1-1, M, 33) with G.J.S. 89-7 (Brazil, Para), G.J.S. 97-178 (Brazil, Para), G.J.S. 93-23 (New Caledonia) and G.J.S. 85-236 (Indonesia, Celebes) produced 16 viable ascsopores (Table 9).

TABLE 9

Sexual crossing of CBS999.97 with non-CBS999.97 isolates

| Sexual crossing | # of asci dissected (# of asci with 4 or 8 inviable ascospores) |
|---|---|
| CBS999.97(1-2, wt; French Guiana) & G.J.S. 86-404(1-1, wt; French Guiana) | 7 (0) |
| CBS999.97(1-2, M, 33; French Guiana) & G.J.S. 86-410(1-1, M, 33; French Guiana) | 8 (0) |
| CBS999.97(1-2, M, 33; French Guiana) & G.J.S. 84-473(1-1, *; French Guiana) | 7 (0) |
| CBS999.97(1-1, M, 33; French Guiana) & G.J.S. 89-7(1-2, M, 33; Brazil, Para) | 7 (0) |
| CBS999.97(1-1, M, 33; French Guiana) & G.J.S. 97-178(1-2, M, 33; Brazil, Para) | 9 (0) |
| CBS999.97(1-1, M, 33; French Guiana) & G.J.S. 93-23(1-2, *; New Caledonia) | 9 (0) |
| CBS999.97(1-1, M, 33; French Guiana) & G.J.S. 85-236(1-2, M, 33; Indonesia Celebes) | 9 (0) |
| CBS999.97(1-1, M, 33; French Guiana) & G.J.S. 85-249(1-1, M, 33; Indonesia Celebes) | 9 (7) |
| CBS999.97(1-2, F, X; French Guiana) & G.J.S. 86-404 (1-1, M, 33; French Guiana) | 9 (8) |
| CBS999.97(1-2, F, X; French Guiana) & G.J.S. 86-410 (1-1, M, 33; French Guiana) | 7 (5) |
| CBS999.97(1-1, F, X; French Guiana) & | 9 |

TABLE 9-continued

Sexual crossing of CBS999.97 with non-CBS999.97 isolates

| Sexual crossing | # of asci dissected (# of asci with 4 or 8 inviable ascospores) |
|---|---|
| G.J.S. 89-7 (1-2, M, 33; Brazil, Para) | (8) |
| CBS999.97(1-1, F, X; French Guiana) & G.J.S. 97-178 (1-2, M, 33) | 8 (6) |
| CBS999.97(1-1, F, X; French Guiana) & G.J.S. 93-23 (1-2, *; New Caledonia) | 8 (4) |
| CBS999.97(1-1, F, X; French Guiana) & G.J.S. 85-236 (1-2, wt; New Caledonia) | 7 (6) |

*: Diagnostic PCR failed to detect M, F, 33 or X in G.J.S. 84-473 and G.J.S. 93-23, respectively.

Therefore, we infer that the ancestral *T. reesei* genomes likely contain scaffold M and Scaffold 33, and that Scaffold F and Scaffold X evolved later in French Guiana via unequal DNA rearrangement between scaffold M and scaffold 33. Intriguingly, these 9 non-CBS999.97 isolates examined here could only sexually cross with CBS999.97(1-1) or CBS999.97(1-2) but not with each other (Table 10).

TABLE 10

| Sexual crossing | Fruiting body |
|---|---|
| G.J.S. 86-410 (1-1, wt; French Guiana) & G.J.S. 89-7 (1-2, wt; Brazil, Para) | — |
| G.J.S. 86-410 (1-1, wt; French Guiana) & G.J.S. 85-229 (1-2, wt; Indonesia, Celebes) | — |
| G.J.S. 84-473 (1-1, wt; French Guiana) & G.J.S. 85-229 (1-2, wt; Indonesia, Celebes) | — |
| G.J.S. 84-473 (1-1, wt; French Guiana) & G.J.S. 93-23 (1-2, wt; New Caledonia) | — |
| G.J.S. 85-249 (1-1, wt; Indonesia, Celebes) & G.J.S. 85-229 (1-2, wt; Indonesia, Celebes) | — |
| G.J.S. 85-249 (1-1, wt; Indonesia, Celebes) & G.J.S. 85-236 (1-2, wt; Indonesia, Celebes) | — |
| G.J.S. 85-249 (1-1, wt; Indonesia, Celebes) & G.J.S. 93-23 (1-2, wt; New Caledonia) | — |

Sequence heterozygosity might also account for the results that sexual crossing of CBS999.97(1-1) with RUT-C30 (FIG. 1D) and QM9414 (FIG. 1E) mostly generated asci with 0 or 4 viable ascospores. As described above, the genomes of these two cellulase-overproducing mutants had acquired numerous mutations, deletions and chromosomal rearrangements via multiple rounds of physical and chemical mutagenesis [2,3].

2.5 Segmentaly Duplication Affects Local and Global Transcription

A hallmark of the QM6a genome is that many genes encoding the carbohydrate-active enzymes (CAZymes) are non-randomly distributed in several gene clusters [1]. The CAZymes can cleave, build and rearrange oligo- and polysaccharides [24]. The majority of the CAZyme genes in these clusters encode glycoside hydrolases that contribute to degradation of lignocelluloses and plant cell walls. Previous transcriptomic studies also showed that adjacent or nearly adjacent genes were coexpressed in four CAZyme gene clusters located in scaffolds 1, 6, 28 and 29 [1]. Notably, the CAZyme gene cluster in scaffold 28 is located at the D segment, and includes an endo-β-1,4-xylanase gene (ID 69276), a β-mannosidase (ID 69245) and the cip2 glucuronoyl esterase gene (ID 123940). The D segment also contains the xyn2 xylanase II gene in scaffold 27 (ID 123818). These four genes all encode enzymes with hemicellulase activity [24]. Indeed, the progeny with two D segments exhibited higher xylanase activities than the euploid progeny or their parental haploid strains did (FIG. 10A).

Next, we examined whether this segmental duplication might affect global transcription by comparing the transcriptomic profiles in five progeny with duplicated segments (D1-5) against those in a parental strain (N0) and six euploid progenies (N1-6). The results of heatmap and clustering analyses revealed that the global transcript profiles in the five strains with duplicated segments are different from those in the seven euploid control strains (FIG. 10B). Strikingly, segmental duplication not only enhanced local transcription of the duplicated genes but also globally promoted transcription of several non-duplicated genes (FIG. 10C). In the 3 SAN strains (D2, D3 and D5) with higher xylanase activities (FIG. 10A), there were 5 CAZymes that exhibited moderate and significant increases in transcription in comparison with those in the six euploid progeny strains (N1-N6; FIG. 10C), including xyn2 (3.5-fold, P=0.010; scaffold 27, ID: 123818), a β-mannosidase (3.4-fold, P=0.019; scaffold 28, ID: 69245), a GH54 α-L-arabinofuranosidase (2.3-fold, P=0.019; scaffold 2, ID: 55319), a candidate GH71 α-1,3-L-glucanase (2.5-fold, P=0.030; scaffold 5, ID: 120873) and cel3d GH3 β-1,3-L-glucanase (1.9-fold, P=0.009; scaffold 5, ID:46816).

In those five segmentally aneuploid strains (D1-5), there were at least 42 annotated or candidate genes (including 23 CAZymes, 7 transcriptional factors, 8 carbohydrate transporters, 4 Gcn5-related N-acetyl transferases) that exhibited at least a 2-folds (p<0.05) increase in transcription in comparison with that in the seven euploid control strains (N0 and N1-6). See Table 11.

TABLE 11

Segmental genome duplication induces local and global transcription enhancement.

| Scaffold | Location in Trire2.0 | Gene ID | Folds increase in mRNA | P value | Gene Copy # | Annotation |
|---|---|---|---|---|---|---|
| 1 | 523039-524216 | *73638 | 2.4 | 0.020 | 1 | cip1, cellulose-binding protein |
| 1 | 524767-526117 | *,#73643 | 2.8 | 0.015 | 1 | elg4/cel61a; endo-glucanase |
| 1 | 2680317-2681029 | #103103 | 4.1 | 0.005 | 1 | Cand. alginate lyase; PL7 |
| 2 | 136228-137636 | 55630 | 4.1 | <0.001 | 1 | Cand. monocarboxylate transporter |
| 2 | 1617508-1619040 | #55319 | 2.6 | 0.016 | 1 | α-L-arabinofuranosidase; GH54 |
| 3 | 173659-174478 | 56587 | 7.5 | <0.001 | 1 | Gcn5-related N-acetyltransferase |
| 3 | 1076400-1077635 | #56996 | 5.1 | 0.111 | 1 | man1; β-mannanase; GH5 |
| 5 | 56670-58956 | #120873 | 2.8 | 0.038 | 1 | Cand. α-1,3-glucanase; GH71 |
| 5 | 13220-15860 | #46816 | 2.1 | 0.019 | 1 | cel3d; Cand. β-glucosidase; GH3 |
| 6 | 100991-103522 | *,#121127 | 5.8 | 0.038 | 1 | bxl1; β-xylosidase; GH3 |
| 6 | 1334204-1335781 | 76910 | 2.5 | 0.001 | 1 | Cand. monocarboxylate transporter |
| 6 | 1311494-1313703 | 106677 | 2.0 | 0.005 | 1 | Cand. fungal transcriptional factor |

TABLE 11-continued

Segmental genome duplication induces local and global transcription enhancement.

| Scaffold | Location in Trire2.0 | Gene ID | Folds increase in mRNA | P value | Gene Copy # | Annotation |
|---|---|---|---|---|---|---|
| 10 | 29531-32375 | #49081 | 3.1 | 0.032 | 1 | cel74a; xyloglucanase; GH74 |
| 12 | 6532-7730 | 108655 | 7.8 | 0.049 | 1 | Cand. β-1,3-exoglucanase (GI:2924313) |
| 13 | 24109-24657 | 4484 | 2.4 | <0.001 | 1 | Gcn5-related N-acetyltransferase |
| 13 | 116709-117959 | 109235 | 6.2 | 0.001 | 1 | carbohydrate-binding module family 18 |
| 15 | 496013-497744 | 109331 | 3.0 | 0.001 | 1 | Cand. cellobiose dehydrogenase (GI: XP_747382.1) |
| 15 | 50427-52658 | 65854 | 2.2 | 0.026 | 1 | Cand. fungal transcriptional factor |
| 19 | 559235-560771 | 66854 | 2.3 | <0.001 | 1 | Cand. monocarboxylate transporter abf1; |
| 19 | 644330-646157 | #123283 | 2.5 | 0.05 | 1 | α-L-arabinofuranosidase I; GH54 |
| 19 | 239605-241110 | 110768 | 4.2 | <0.001 | 1 | Cand. monocarboxylate transporter |
| 22 | 293398-294325 | 111094 | 4.9 | <0.001 | 1 | carbohydrate-binding module family 13 |
| 24 | 56135-56903 | 123668 | 4.4 | <0.001 | 1 | Gcn5-related N-acetyltransferase |
| 25 | 41968-45217 | 111446 | 2.4 | <0.001 | 2 | Cand. fungal transcriptional factor |
| 27 | 67980-69419 | 69164 | 2.2 | <0.001 | 2 | Cand. monocarboxylate transporter xyn2; |
| 27 | 125447-126445 | #123818 | 8.1 | 0.004 | 2 | endo-β-1,4-xylanase; GH11 |
| 27 | 193632-195569 | 68930 | 2.5 | <0.001 | 2 | Cand.C6 transcriptional factor |
| 27 | 207908-209899 | 111515 | 2.3 | <0.001 | 2 | Cand. fungal transcriptional factor |
| 27 | 210428-211052 | 72524 | 4.0 | <0.001 | 1 | basic leucine zipper transcription factor |
| 28 | 244151-246792 | #72526 | 2.4 | 0.054 | 1 | glr1; α-glucuronidase; GH67 |
| 28 | 376804-378261 | *,#69276 | 8.1 | 0.049 | 2 | Cand. endo-β-1,4-xylanase; GH30 |
| 28 | 380280-381719 | *,#123940 | 6.8 | 0.047 | 2 | cip2; glucuronoyl esterase; CE15 |
| 28 | 386646-389732 | *,#69245 | 4.4 | 0.013 | 2 | Cand. β-mannosidase; GH2 |
| 28 | 263357-264915 | *69574 | 3.5 | <0.001 | 1 | Cand. monocarboxylate transporter |
| 29 | 342967-344755 | *123992 | 2.2 | 0.092 | 1 | swollenin |
| 29 | 346861-348532 | *,#111849 | 2.0 | 0.019 | 1 | xyn4; endo-β-1,4-xylanase; GH30 |
| 29 | 16492-18014 | 69771 | 2.7 | 0.004 | 1 | Cand. monocarboxylate transporter |
| 30 | 179270-181052 | 69957 | 5.6 | 0.037 | 1 | Cand. carbohydrate permease |
| 33 | 83592-84140 | 70201 | 2.7 | 0.001 | 1 | Cand. GCN5-related N-acetyltransferase |
| 33 | 880358-8936 | #112140 | 2.9 | 0.033 | 1 | pgx1; Cand. exo-polygalacturonase; GH28 |
| 33 | 10241-14095 | 71072 | 3.2 | 0.017 | 1 | gluconate kinase |
| 50 | 6230-7984 | 36913 | 3.0 | <0.001 | 1 | Cand. fungal transcriptional factor |

*Genes in the CAZyme gene clusters of scaffolds 1, 6, 28 and 29 are indicated (Martinez et al, 2008).
The CAZyme genes are annotated as described lately, including glycoside hydrolase genes (GHs), carbohydrate esterases (CEs) and polysaccharide lyases (PLs) (Hakkinen et al, 2012).

2.6 Segmental Duplication Provides Growth Advantage on a Xylan-Based Medium

Changes in DNA copy number are largely detrimental [25]. The aCGH results indicate that the SAN progeny generated from wild-type CBS999.97 always returned to the euploid state after 2-3 weeks of vegetative propagation in a dextrose-rich medium (FIG. 11A). Studies in several microorganisms also reveal that DNA copy-number alterations can be beneficial, increasing survival under selective pressure [8,11,12,25-30]. We found that, when grown on a xylan-based medium, the SAN mutants produced more biomass on a xylan-based medium than the parental CBS999.97 euploid strain and the return-to-euploid (RTU) mutants did (FIG. 11B). Given the lack of the L segment in the RTU mutants (FIG. 9, the two bottom panels), we conclude that D segment duplication, but not L segment deletion, is responsible for the growth advantage in the xylan-based medium. Intriguingly, the SAN strain also grew better than the CBS999.97 euploid haploid on rice straw (FIG. 11C). Together, these results suggest that meiosis-driven segmental duplication apparently provides an advantage to transiently enhance efficiency in degrading and utilizing lignocellulosic biomass.

2.7 Deletion of NHEJ Gene Prevents SAN Returning to Euploidy

Remarkably, we discovered that deletion of tku70 or tmus53 could stabilize segmental duplication up to >7 weeks (FIG. 11A). We also showed that two tmus53Δ SAN mutant (WTH1994 and WTH4503) not only generated more biomass than both wild-type and tmus53Δ euploid strains (FIG. 11B) but also maintained high production of hemicellulases up to >7 weeks (FIG. 11D), indicating that NHEJ, not homologous recombination, mediates restoration to euploidy. The tmus53Δ SAN strain (WTH1994), compared to the industrial strain RUT-C30, secreted >2.0-fold xylanases (FIG. 11E) as well as ~0.8-fold cellulases (FIG. 11F), respectively. Consistent with previous results [31], RUT-C30 secreted ~3-fold more cellulases than QM6a did (FIG. 11F). These results indicate that the tmus53Δ SAN mutants have useful potentials for industrial application.

TABLE 12

Loss of non-homologous end joining gene prevents the segmental aneuploidy (SA) returning to euploidy (E)[1].

| Days after vegetative propagation in MEA medium | Wild-type (D2) | Wild-type (D3) | Δku70 | Δmus53 |
|---|---|---|---|---|
| 14 | SAN | SAN | SAN | SAN |
| 24 | E | SAN | SAN | SAN |
| 34 | E | E | SAN | SAN |
| 50 | [2]N.D. | N.D. | SAN | SAN |

[1]Segemtal aneploidy (SAN) and euploidy (E) were determined by array-based comparative genomic hybridization (aCGH) experiments.
[2]ND: not determined.

3. Summary and Discussion

The current study reveals at least 5 novel characteristics of *T. reesei* sexual development and genome plasticity.

First, *T. reesei* generates asci with 16-part ascospores [4] via meiosis and two further rounds of mitotic nuclear divisions. Intriguingly, most other ascomycote fungi generate asci with 4 ascospores (e.g., *S. cerevisiae*) via meiosis or 8 ascospores (e.g., *Neurospora crassa*) via meiosis and one round of postmeiotic division, respectively.

Second, like several other filamentous fungi, the sexually competent CBS999.99 wild isolate frequently generated inviable ascopores. Given that sexual crossing between two homeologous haploid strains (e.g., CBS999.97) can occur in natural environments and that chromosome heterozygosity of the two CBS999.97 haploid genomes is responsible for production of inviable ascospores, it is of interest to propose that *T. reesei* might overcome such a disadvantage by increasing the overall ascospore number per ascus via two rounds of postmeiotic divisions.

Third, our results indicate that the genome of ancestral *T. reesei* genomes, like that of CBS999.97, contain scaffold M and Scaffold 33. Scaffold X and Scaffold F in CBS999.9(1-1) haploid genome were likely generated via an unequal DNA rearrangement between Scaffold M and Scaffold 33. Accordingly, we speculate that the genome of G.J.S. 85-249 (1-1, M, 33) might contain different homeologous sequences or rearrangements in other chromosomal region(s), because sexual crossing of G.J.S. 85-249 (1-1, M, 33) with either CBS999.97(1-1, M, 33) or CBS999.97(1-2, F, X) resulted in asci with 4, 8 or 12 inviable ascospores (Table 2). By sexual crossing two haploid strains with chromosome heterozygosity (one containing scaffold 33+M and the other containing scaffold F+X), a SAN progeny with duplication of D segment which exhibit enhanced expression level or enzymatic activities of carbohydrate-active enzymes (CAZymes) or increased biomass production can be produced.

Fourth, many *Trichoderma* species are found as anamorphs that present in soils, where they act as plant beneficial fungi [32]. In contrast, the telomorphic *Hypocrea* species are most frequently found on decorticated wood or wood rotting fungi (e.g., wood ear, shelf fungi or agarics). With better capability in lignocellulosic biomass degradation, the SAN sexual progeny we described in this report likely can provide adaptive advantages to the natural environments, especially in the early phase of colonization (the first two weeks of growth).

Lastly, a key finding of this report is that deletion of NHEJ genes can prevent the SAN progeny from returning to euploidy. Studies in several microorganisms and mammalian cells reveal that SAN and aneuploidy are known to cause a proliferative disadvantage in most normal cells. Unless under selective pressure or in condition associated with improved proliferative abilities (e.g., cancer cells), the SAN and aneuploid cells would readily undergo RTU [8,25, 27-30]. It was reported that ubiquitin-proteasomal degradation has an important role in suppressing the adverse effects of SAN and aneuploidy [33], it is still unclear which DNA repair and/or recombination machinery is involved in RTU. Our results here demonstrate that the NHEJ repair pathway plays a role in promoting RTU in *T. reesei*. A surprising outcome of this study is to the finding that the tmus53Δ SAN mutants have a promising industrial potential for increased lignocellulosic biomass degradation.

```
                         Sequence Information

Primer A (SEQ ID NO: 1)
5'-CTTCCAGCCTAAGTACTC-3'

Primer B (SEQ ID NO: 2)
5'-GTCGATCGTGCTAATGAAG-3'

Primer C (SEQ ID NO: 3)
5'-CAAGGCTATTATCCGCAG-3'

Primer D (SEQ ID NO: 4)
5'-CTCTGAGGGGATTAGAAG-3'

Amplified fragment by primers C and B (SEQ ID NO: 5)
(547 bp, corresponding to scaffold 33: 32892-33438 bp)
Primers C + B
CAAGGCTATTATCCGCAGTGGGACAATTGTGCTTTGATGTTGGTTCGCTCTACACTG
GGTCAAACATGAACAGGCAGTGGAGGGGGGTGTGATGAGAATGAAACCAAGAGCCAA
CCTGTGGATCAATTTCAACGTGGGGCGATGTGCATGTAGGGACTCCGAAGTGTTTTC
GGGACGGAACCGGCCTAAACAAGACCATGTTCGACGGTTTATTAAGCAGGCAAATAT
CGACAGGCATGGCGTATGTCAAGACCTAATCAATCATTGTCCTGGTGAGGCCTATAC
CTGCCGTTGTGGAAAGATACTCGCGATGTATTTTTTCTTCTGTCTCTGTCATCGAT
ACTTGCCTACTGGATCATCAAGACGGCCGTCTCTTCAAACAAAGATCGACTTTATGC
CCGCCGAAAAGCATGTCAACCCTGCGCGCGCCTACCACAAACTGAAAGGGTCATTGG
CTATTCTTTGTTCAAGCAAGATGCTACCATTGCACGCCAGGGGAGGTCCTTGCAAAC
AGCCCAAGACCGCTTCCGTTTGCTCGGTGACACG Amplified fragment by primers A and D (SEQ ID NO: 6)
(467 bp, corresponding to scaffold 36: 54048-54514 bp)
Primers A + D
CTTCCAGCCTAAGTACTCTGCTAAAGGGCGTATCTTGTAATGTATACTTTAACTGTT
ACTGCATTGTAAAGCCAAACACTGCGGGCTTCCATATGGGAAATTGATCTATCTCAA
TAGCGCTCAGTAGGTACGAAGAGTAGGCATCCCTCGAGACAAACCCTCCTCCACGAG
CCCCTCAAGTGGTAGGTAGTTCAGGTGCACTCTGCACGAACGCTGACTGCACATCAG
ACGCACTTGGTGCTGATTCTCGCTGCAGAGGAGTGAGGTACCCGTATCACCCTACTC
CAATCGCCTGAGAAGCTTGTATCTTGCTCAACATTCCGGAGCAGCACCTACATGTAC
TACATGTGAATCGCCCTATATCTCATTCTGACCGGAGAACGAGACAGCACCCACGTA
TTCATACCTATTTACTTTCTTCTGTTTTTTACCTCTTCTCGATCTTCTTTTCTTCTA
ATCCCCTCAGA
```

Sequence Information

Amplified fragment by primers A and B (SEQ ID NO: 7)
(462 bp, corresponding to scaffold 36: 54048-54320 bp (underline)
plus scaffold 33: 33250-33438 by (double underline))
Primers A + B
CTTCCAGCCTAAGTACTCTGCTAAAGGGCGTATCTTGTAATGTATACTTTAACTGTT
ACTGCATTGTAAAGCCAAACACTGCGGGCTTCCATATGGGAAATTGATCTATCTCAA
TAGCGCTCAGTAGGTACGAAGAGTAGGCATCCCTCGAGACAAACCCTCCTCCACGAG
CCCCTCAAGTGGTAGGTAGTTCAGGTGCACTCTGCACGAACGCTGACTGCACATCAG
ACGCACTTGGTGCTGATTCTCGCTGCAGAGGAGTGAGGTACCCGTATCAAGACGGCC
GTCTCTTCAAACAAAGATCGACTTTATGCCCGCCGAAAAGCATGTCAACCCTGCGCG
CGCCTACCACAAACTGAAAGGGTCATTGGCTATTCTTTGTTCAAGCAAGATGCTACC
ATTGCACGCCAGGGGAGGTCCTTGCAAACAGCCCAAGACCGCTTCCGTTTGCTCGGT
GACACG Amplified fragment by primers C and D (SEQ ID NO: 8)
(552 bp, corresponding to scaffold33: 32892-33249 by (underline)
plus scaffold 36: 54321-54514 by (double underline))
Primers C + D
CAAGGCTATTATCCGCAGTGGGACAATTGTGCTTTGATGTTGGTTCGCTCTACACTG
GGTCAAACATGAACAGGCAGTGGAGGGGGGTGTGATGAGAATGAAACCAAGAGCCAA
CCTGTGGATCAATTTCAACGTGGGGCGATGTGCATGTAGGGACTCCGAAGTGTTTTC
GGGACGGAACCGGCCTAAACAAGACCATGTTCGACGGTTTATTAAGCAGGCAAATAT
CGACAGGCATGGCTATGTCAAGACCTAATCAATCATTGTCCTGGTGAGGCCTATAC
CTGCCGTTGTGGAAAGATACTCGCGATGTATTTTTTCTTCTGTCTCTGTCATCGAT
ACTTGCCTACTGGATCATCACCCTACTCCAATCGCCTGAGAAGCTTGTATCTTGCTC
AACATTCCGGAGCAGCACCTACATGTACTACATGTGAATCGCCCTATATCTCATTCT
GACCGGAGAACGAGACAGCACCCACGTATTCATACCTATTTACTTTCTTCTGTTTTT
TACCTCTTCTCGATCTTCTTTTCTTCTAATCCCCTCAGA Nucleotide sequence of the DNA probe (SEQ ID NO: 9)
AGCTACATGAGATCCTGCATACCGTATCTTTGTCCTGGTAAACTATTGTTTCGTAGT
TCAAGAGGACATTCTGAAGGAACACCGAGAGCATTTCTTCCAGCCTAAGTACTCTGC
TAAAGGGCGTATCTTGTAATGTATACTTTAACTGTTACTGCATTGTAAAGCCAAACA
CTGCGGGCTTCCATATGGGAAATTTTCTTATTTCAATAGCGCTCAGTAGGTACGAAG
AGTAGGCATCCCTCGAGACAAACCCTCCTCCACGAGCCCCTCAAGTGGTAGGTAGTT
CAGGTGCACTCTGCACGAA Primer PA7543 (SEQ ID NO: 10)
AGCTACATGAGATCCTGCAT Primer A7544 (SEQ ID NO: 11)
TCAGGTGCACTCTGCACGAA Nucleotide sequence of the 443bp band (SEQ ID NO: 12)
TTAAATCCCACAACTACCTATTACTACATGTACATTTGATCAATTGCAAGCCGTGAC
CGAGCTACATGAGATCCTGCATACCGTATCTTTGTCCTGGTAAACTATTGTTTCGTA
GTTCAAGAGGACATTCTGAAGGAACACCGAGAGCATTTCTTCCAGCCTAAGTACTCT
GCTAAAGGGCGTATCTTGTAATGTATACTTTAACTGTTACTGCATTGTAAAGCCAAA
CACTGCGGGCTTCCATATGGGAAATTTTCTTATTTCAATAGCGCTCAGTAGGTACGA
AGAGTAGGCATCCCTCGAGACAAACCCTCCTCCACGAGCCCCTCAAGTGGTAGGTAG
TTCAGGTGCACTCTGCACGAACGCTGACCGCACATCAGACGCACTTGGTGCTGATTC
TCGCTGCAGAGGAGCGAGGTACCCCTATCAAGACGGCCGTCTCT Nucleotide sequence of the 1512bp band (SEQ ID NO: 13)
TTAAATCCCACAACTACCTATTACTACATGTACATTTGATCAATTGCAAGCCGTGAC
CGAGCTACATGAGATCCTGCATACCGTATCTTTGTCCTGGTAAACTATTGTTTCGTA
GTTCAAGAGGACATTCTGAAGGAACACCGAGAGCATTTCTTCCAGCCTAAGTACTCT
GCTAAAGGGCGTATCTTGTAATGTATACTTTAACTGTTACTGCATTGTAAAGCCAAA
CACTGCGGGCTTCCATATGGGAAATTTTCTTATTTCAATAGCGCTCAGTAGGTACGA
AGAGTAGGCATCCCTCGAGACAAACCCTCCTCCACGAGCCCCTCAAGTGGTAGGTAG
TTCAGGTGCACTCTGCACGAACGCTGACCGCACATCAGACGCACTTGGTGCTGATTC
TCGCTGCAGAGGAGCGAGGTACCCCTATCACCCTACTCCAATCGCCTGAGAAGCTTG
TATCTTGCTCAACATTCCGGAGCAGCACCTACATGTACTACATGTGAATCGCCCTAT
ATCTCATTCTGACCGGCGAACGAGACAGCACCCACCACGTATTCATGCCTATTTACT
TTCTTCTGTATTTTACCTCTTCTCGATCTTCTTTTCTTCTAATCCCCTCAGAGCCTC
AACAACCTCCACCTCTTTCTGCATCAGCACACGAGTGACATCCTGCATCTTCCACAC
CATCAGATACGTTGGTCCTCCTTTTAAGAAAGCTACAAAACTTGTAAGAAATCTTCA
CTTAAGGTACTGAGAGGTTCTTGTTTCTTTATGCTACAGTCCTTCGAGATAACTGAC
ACATAGTGTTTCATTCAGCATCGCTTCCATTGCGCTCGTTTTCTCGGCTCACCTCAA
AGACATCTCAGCCATCTTGGAGGCCAAGAGCAAGATATCAAACAATCTTCTCTTTGA
ACTGGTGGCAATGAGCAGCGATAGCTATTGGATTGTTCCTCCTCAACCCCCGGGTGG
TGGCACGTGGAAAGGCTGTGCTCTGCTCAAGAAGCCAGATGGAGGAGATTTCGTGCT
ATTTTCTCCCAATGCCGTGCATCTGAGTGCGATGCTCCAGGTGCATGACGCGCACCA

Sequence Information

```
AGCATCTGTCGTCAGTAATGCATCTCAGTCGACCTCACAAGACAATGAGATGACTGA
GTTCATGGTAATGGGACGATGCAGACATTTGTTGGATGGCTATTCGCACACGAACCC
TCAAAGCTCATCCGGACAAATGGCAGAGAGCTTGAACAGGCTACATGCCGATTTGAA
AGGAACAAGGTCCCGAGGGCAGAAGTTCATCACTGCAGCATACGTCGGCTTCGACTC
CTGCATGCAGGGTCCTGTCTTTGCCAGGGCGGCTAAAGATGCGGCCAGCTCCAACCC
CTCCAAATCGATCGCTTCGAATGAAGCAAATCAGTCAAGAGGGTCAAACGGTATCCT
TGACCTGAAGGATCTGAGCTTCAGTTGTGGCTCTGCGTCCTCTTCTGTGGGACTGGG
ATTCATTCCACATTATGCAGTAACGTCTCG
```

REFERENCES

1. Martinez D, Berka R M, Henrissat B, Saloheimo M, Arvas M, et al. (2008) Genome sequencing and analysis of the biomass-degrading fungus *Trichoderma reesei* (syn. *Hypocrea jecorina*). Nat Biotechnol 26: 553-560.
2. Peterson R, Nevalainen H (2012) *Trichoderma reesei* RUT-C30-thirty years of strain improvement. Microbiology 158: 58-68.
3. Vitikainen M, Arvas M, Pakula T, Oja M, Penttila M, et al. (2010) Array comparative genomic hybridization analysis of *Trichoderma reesei* strains with enhanced cellulase production properties. BMC Genomics 11: 441.
4. Samuels G J, Petrini O, Manguin S (1994) Morphological and macromolecular characterization of *Hypocrea schweinitzii* and its *Trichoderma* anamorph. Micologia 86: 421-435.
5. Seidl V, Seibel C, Kubicek C P, Schmoll M (2009) Sexual development in the industrial workhorse *Trichoderma reesei*. Proc Natl Acad Sci USA 106: 13909-13914.
6. Cole F, Keeney S, Jasin M (2010) Evolutionary conservation of meiotic DSB proteins: more than just Spo11. Genes Dev 24: 1201-1207.
7. Fraser J A, Huang J C, Pukkila-Worley R, Alspaugh J A, Mitchell T G, et al. (2005) Chromosomal translocation and segmental duplication in *Cryptococcus neoformans*. Eukaryot Cell 4: 401-406.
8. Ni M, Feretzaki M, Li W, Floyd-Averette A, Mieczkowski P, et al. (2013) Unisexual and heterosexual meiotic reproduction generate aneuploidy and phenotypic diversity de novo in the yeast *Cryptococcus neoformans*. PLoS Biol 11: e1001653.
9. Wittenberg A H, van der Lee T A, Ben M'barek S, Ware S B, Goodwin S B, et al. (2009) Meiosis drives extraordinary genome plasticity in the haploid fungal plant pathogen *Mycosphaerella graminicola*. PLoS One 4: e5863.
10. Goodwin S B, M'Barek S B, Dhillon B, Wittenberg A H, Crane C F, et al. (2011) Finished genome of the fungal wheat pathogen *Mycosphaerella graminicola* reveals dispensome structure, chromosome plasticity, and stealth pathogenesis. PLoS Genet 7: e1002070.
11. Tegtmeier K J, VanEtten H (1982) Genetic studies on selected traits of *Nectria haematococca*. Phytopathology 72: 604-607.
12. Taga M, Murata M, VanEtten H D (1999) Visualization of a conditionally dispensable chromosome in the filamentous ascomycete *Nectria haematococca* by fluorescence in situ hybridization. Fungal Genet Biol 26: 169-177.
13. Coleman J J, Rounsley S D, Rodriguez-Carres M, Kuo A, Wasmann C C, et al. (2009) The genome of *Nectria haematococca*: contribution of supernumerary chromosomes to gene expansion. PLoS Genet 5: e1000618.
14. Schmoll M, Seibel C, Tisch D, Dorrer M, Kubicek C P (2010) A novel class of peptide pheromone precursors in ascomycetous fungi. Mol Microbiol 77: 1483-1501.
15. Chen C L, Kuo H C, Tung S Y, Hsu P W, Wang C L, et al. (2012) Blue light acts as a double-edged sword in regulating sexual development of *Hypocrea jecorina* (*Trichoderma reesei*). PLoS One 7: e44969.
16. Guangtao Z, Hard L, Schuster A, Polak S, Schmoll M, et al. (2009) Gene targeting in a nonhomologous end joining deficient *Hypocrea jecorina*. J Biotechnol 139: 146-151.
17. Steiger M G, Vitikainen M, Uskonen P, Brunner K, Adam G, et al. (2011) Transformation system for *Hypocrea jecorina* (*Trichoderma reesei*) that favors homologous integration and employs reusable bidirectionally selectable markers. Appl Environ Microbiol 77: 114-121.
18. Tisch D, Kubicek C P, Schmoll M (2011) The phosducin-like protein PhLP1 impacts regulation of glycoside hydrolases and light response in *Trichoderma reesei*. BMC Genomics 12: 613.
19. Penttila M, Nevalainen H, Ratto M, Salminen E, Knowles J (1987) A versatile transformation system for the cellulolytic filamentous fungus *Trichoderma reesei*. Gene 61: 155-164.
20. Mantyla A L, Rossi K H, Vanhanen S A, Penttila M E, Suominen P L, et al. (1992) Electrophoretic karyotyping of wild-type and mutant *Trichoderma longibrachiatum* (*reesei*) strains. Curr Genet 21: 471-477.
21. Herrera-Estrella A, Goldman G H, van Montagu M, Geremia R A (1993) Electrophoretic karyotype and gene assignment to resolved chromosomes of *Trichoderma* spp. Mol Microbiol 7: 515-521.
22. Jung M K, Ovechkina Y, Prigozhina N, Oakley C E, Oakley B R (2000) The use of beta-D-glucanase as a substitute for Novozym 234 for immunofluorescence and protoplasting. Fungal Genet Newsletter 47: 65-66.
23. Lieckfeldt E, Kullnig C, Samuels G J, Kubicek C P (2000) Sexually competent, sucrose- and nitrate-assimilating strains of *Hypocrea jecorina* (*Trichoderma reesei*) from South American soils. Mycologia 92: 374-380.
24. Hakkinen M, Arvas M, Oja M, Aro N, Penttila M, et al. (2012) Re-annotation of the CAZy genes of *Trichoderma reesei* and transcription in the presence of lignocellulosic substrates. Microb Cell Fact 11: 134.
25. Tang Y C, Amon A (2013) Gene copy-number alterations: a cost-benefit analysis. Cell 152: 394-405.
26. Gresham D, Desai M M, Tucker C M, Jenq H T, Pai D A, et al. (2008) The repertoire and dynamics of evolutionary adaptations to controlled nutrient-limited environments in yeast. PLoS Genet 4: e1000303.
27. Ni M, Feretzaki M, Sun S, Wang X, Heitman J (2011) Sex in Fungi. Annu Rev Genet 45: 405-430.
28. Sheltzer J M, Amon A (2011) The aneuploidy paradox: costs and benefits of an incorrect karyotype. Trends Genet 27: 446-453.

29. Chen G, Bradford W D, Seidel C W, Li R (2012) Hsp90 stress potentiates rapid cellular adaptation through induction of aneuploidy. Nature 482: 246-250.
30. Chang S L, Lai H Y, Tung S Y, Leu J Y (2013) Dynamic large-scale chromosomal rearrangements fuel rapid adaptation in yeast populations. PLoS Genet 9: e1003232.
31. Ghosh A, Ghosh B K, Trimino-Vazquez H, Eveleigh D E, Montenecourt B S (1984) Cellulase secretion from a hyper-cellulolytic mutant of *Trichoderma reesei* Rut-C30. Arch Microbiol 140: 126-133.
32. Mukherjee P K, Horwitz B A, Herrera-Estrella A, Schmoll M, Kenerley C M (2013) *Trichoderma* research in the genome era. Annu Rev Phytopathol 51: 105-129.
33. Tones E M, Dephoure N, Panneerselvam A, Tucker C M, Whittaker C A, et al. (2010) Identification of aneuploidy-tolerating mutations. Cell 143: 71-83.

What is claimed is:

1. A method for preparing a segmental aneuploid strain of *Trichoderma reesei* comprising steps of:
   (a) identifying and choosing a first strain being *Trichoderma reesei*, which is mating competent and carries scaffold 33 and scaffold M in its genome;
   (b) identifying and choosing a second strain being *Trichoderma reesei*, which is mating competent, capable of mating with the first strain of step (a), and carries scaffold F and scaffold X in its genome;
   (c) sexually crossing the first strain of step (a) with the second strain of step (b); and
   (d) identifying and selecting a segmental aneuploid (SAN) progeny from step (c) that has duplication of the D segment in its genome.

2. The method of claim 1, wherein
   scaffold 33 comprises:
      (i) 5' terminus of scaffold 33 of about 33 kb (referred to as L segment), and
      (ii) 3' terminus of scaffold 33 of about 171 kb (referred to as 33(3') segment);
   scaffold M comprises:
      (i) D segment comprising:
         3' terminus of scaffold 28 of about 37 kb in length (referred to as 28(3') fragment),
         entire scaffold 27 of about 427 kp in length, and
         5' terminus of scaffold 36 of about 52 kb in length (referred to as 36(5') fragment), and
      (ii) a non-D segment comprising:
         3' terminus of scaffold 36 of about 83 kb in length (referred to as 36(3') fragment), and
         5' terminus of scaffold 28 of about 370 kb in length (referred to as "28(5') fragment");
   scaffold F comprises:
      (i) the D segment and
      (ii) the 33(3') segment; and
   scaffold X comprises:
      (i) the L segment and
      (ii) the non-D segment.

3. The method of claim 1, wherein the first strain has a MAT1-1 locus and the second strain has a MAT1-2 locus, or the first strain has a MAT1-2 locus and the second strain has a MAT1-1 locus.

4. The method of claim 1, wherein in step (a), the first strain is identified by conducting a polymerase chain reaction (PCR) analysis to determine the presence of scaffold 33 and scaffold M in its genome.

5. The method of claim 4, wherein the PCR analysis is conducted using a first primer set comprising primer C of SEQ ID NO: 3 and primer B of SEQ ID NO: 2 to determine the presence of scaffold 33, or using a second primer set comprising primer A of SEQ ID NO: 1 and primer D of SEQ ID NO: 4 to confirm the presence of scaffold M, in the first strain's genome.

6. The method of claim 1, wherein in step (b), the second strain is identified by conducting a polymerase chain reaction (PCR) analysis to determine the presence of scaffold F and scaffold X in its genome.

7. The method of claim 6, wherein the PCR analysis is conducted using a third primer set comprising primer A of SEQ ID NO: 1 and primer B of SEQ ID NO: 2 to confirm the presence of scaffold F, or using a four primer set comprising primer C of SEQ ID NO: 3 and primer D of SEQ ID NO: 4 to confirm the presence of scaffold X, in the second strain's genome.

8. The method of claim 1, wherein in step (d), the SAN progeny is identified by a comparative genomic hybridization (CGH) analysis or a Southern blotting analysis to determine duplication of the D segment.

9. The method of claim 8, wherein the Southern blotting analysis is conducted using a probe comprising SEQ ID NO: 9.

10. The method of claim 1, wherein the SAN progeny exhibits enhanced gene expression of one or more genes encoding a carbohydrate-active enzyme (CAZyme).

11. The method of claim 10, wherein the CAZyme-encoding gene is selected from the group consisting of an endo-β-1,4-xylanase gene (xyn2; ID: 123818) at scaffold 27, a β-mannosidase gene (ID: 69245) at scaffold 28, a α-L-arabinofuranosidase gene (GH54, ID: 55319) at scaffold 2, a GH71 α-1,3-L-glucanase gene (GH71, ID: 120873) at scaffold 5, and a β-1,3-L-glucanase gene (cel3d, GH3, ID:46816) at scaffold 5.

12. The method of claim 1, wherein the SAN progeny exhibits enhanced xylanase activities, or increased biomass production on a xylan-based media.

13. The method of claim 1, wherein the first strain or the second strain further include deletion of a non-homologous end joining (NHEJ) gene.

14. The method of claim 13, wherein the resultant SAN progeny, produced from sexual crossing of the first strain and the second strain, having duplication of the D segment and deletion of the NHEJ gene in its genome, is identified and selected.

15. The method of claim 13, wherein the NHEJ gene is tku70 or tmus53.

16. The method of claim 13, wherein the SAN progeny maintains segmental duplication for two weeks, three weeks, four weeks, five weeks, six weeks, or seven weeks or more.

17. A method of producing a stable, segmentally aneuploid strain of *Trichoderma reesei*, comprising:
   (a) sexually crossing two haploid mating competent strains of *Trichoderma reesei* with chromosome heterozygosity, wherein at least one of the strains includes deletion of a NHEJ gene; and
   (b) identifying and selecting a progeny from step (a) that is segmental aneuploid (SAN) and has deletion of the NHEJ gene.

18. The method of claim 17, wherein the NHEJ gene is tku70 or tmus53.

19. The method of claim 17, wherein one of the two mating competent haploid strains carries scaffold 33 and scaffold M, and the other carries scaffold F and scaffold X.

20. The method of claim 19, wherein the SAN progeny from step (a) that includes duplication of D segment and deletion of the NHEJ gene is identified and selected.

21. A stable, segmentally aneuploid strain of *Trichoderma reesei* obtained from claim 17.

22. A stable, segmentally aneuploid strain of *Trichoderma reesei*, which comprises in its genome duplication of D segment and deletion of tku70 or tmus53.

\* \* \* \* \*